(12) United States Patent
Horlick et al.

(10) Patent No.: US 6,417,002 B1
(45) Date of Patent: *Jul. 9, 2002

(54) METHOD FOR MAINTENANCE AND SELECTION OF EPISOMES

(75) Inventors: Robert A. Horlick, Plainsboro, NJ (US); Daniel Chelsky, Montreal (CA)

(73) Assignee: Pharmacopeia, Inc., Cranbury, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/249,585

(22) Filed: Feb. 11, 1999

(51) Int. Cl.$^7$ .................. C12N 15/63; C12N 15/85; C12N 15/87; C12N 5/00; C12N 5/02
(52) U.S. Cl. .................. 435/455; 435/6; 435/320.1; 435/325; 435/369; 435/467; 530/350
(58) Field of Search ................ 435/6, 369, 467, 435/320.1, 325, 455; 530/350

(56) References Cited

U.S. PATENT DOCUMENTS

| | | |
|---|---|---|
| 4,686,186 A | 8/1987 | Sugden |
| 5,707,830 A | 1/1998 | Calos |
| 5,976,807 A * | 11/1999 | Horlick et al. ............ 435/6 |

FOREIGN PATENT DOCUMENTS

| | | |
|---|---|---|
| WO | WO 98/07876 | 2/1998 |

OTHER PUBLICATIONS

Horlick et al., "Combinatorial gene expression using multiple episomal vectors," Gene. Feb. 2000, vol. 243, No. 1–2, pp. 187–194.

Database Caplus, An 1997: 124965, Muecke et al., "Suitability of Epstein–Barr Virus–Based Episomal Vectors for Expression of Cytokine Genes in Human Lymphoma Cells," Abstract, Gene Therapy, vol. 4 No. 2, pp. 82–92.

Kinsella et al., "Episomal Vectors Rapidly and Stably Produce High–Titer Recombinant Retrovirus," Human Gene Therapy, Aug. 1, 1996, vol. 7, pp. 1405–1413.

Horlick et al., Rapid Generation of Stable Cell Lines Expressing Corticotropin–Releasing Hormone Receptor for Drug Discovery, *Protein Expression and Purification* 9, pp. 301–308 (1997), Article No. PT960701.

Damaj et al., Identification of G–protein Binding Sites of the Human Interleukin–8 Receptors by Functional Mapping of the Intracellular Loops, *The FASEB Journal*, vol. 10, pp. 1426–1434, Oct. 1996.

Mellado et al., The Chemokine Monocyte Chemotactic Protein 1 Triggers Janus Kinase 2 Activation and Tyrosine Phosphyorylation of the CCR2B Receptor, *The American Association of Immunologists*, vol. 161, No. 2, pp. 805–813, Jul. 1998.

Sambrook et al., *Molecular Cloning a Laboratory Manual*, pp. 16.17–16.21, 16.28, 1989.

Horlick et al, 1997, Protein Purification and Expression, 9: 301–308.*

Kelekar et al, 1997, Mol. Cell. Biol., 17: 7040–7046.*

Yang et al, 1995, Cell, 80:285–291.*

Wang et al, 1999, Science, 284: 339–343.*

* cited by examiner

*Primary Examiner*—Deborah J. R. Clark
*Assistant Examiner*—Peter Paras, Jr.
(74) *Attorney, Agent, or Firm*—Heslin Rothenberg Farley & Mesiti P.C.

(57) ABSTRACT

A method for obtaining a eukaryotic cell transfected with an episome involves transfecting the cell with the episome under conditions wherein cells survive that are successfully transfected with the episome. The resulting cells express both a first protein whose expression causes cell death and a second protein whose expression prevents cell death resulting from expression of the first protein.

20 Claims, 12 Drawing Sheets

Sequence of EBV oriP

```
GCATGCAGGAAAAGGACAAGCAGCGAAAATTCACGCCCCCTTGGGAGGTGGCGGCATATGCAAAGGATAGCACTCCCACT
CTACTACTGGGTATCATATGCTGACTGTATATGCATGAGGATAGCATATGCTACCCGGATACAGATTAGGATAGCATATA
CTACCCAGATATAGATTAGGATAGCATATGCTACCCAGATATAGATTAGGATAGCCTATGCTACCCAGATATAAATTAGG
ATAGCATATACTACCCAGATATAGATTAGGATAGCATATGCTACCCAGATATAGATTAGGATAGCCTATGCTACCCAGAT
ATAGATTAGGATAGCATATGCTACCCAGATATAGATTAGGATAGCATATGCTATCCAGATATTTGGGTAGTATATGCTAC
CCAGATATAAATTAGGATAGCATATACTACCCTAATCTCTATTAGGATAGCATATGCTACCCGGATACAGATTAGGATAG
CATATACTACCCAGATATAGATTAGGATAGCATATGCTACCCAGATATAGATTAGGATAGCCTATGCTACCCAGATATAA
ATTAGGATAGCATATACTACCCAGATATAGATTAGGATAGCATATGCTACCCAGATATAGATTAGGATAGCCTATGCTAC
CCAGATATAGATTAGGATAGCATATGCTATCCAGATATTTGGGTAGTATATGCTACCCATGGCAACATTAGCCCACCGTG
CTCTCAGCGACCTCGTGAATATGAGGACCAACAACCCTGTGCTTGGCGCTCAGGCGCAAGTGTGTGTAATTTGTCCTCCA
GATCGCAGCAATCGCGCCCCTATCTTGGCCCGCCCACCTACTTATGCAGGTATTCCCCGGGGTGCCATTAGTGGTTTTGT
GGGCAAGTGGTTTGACCGCAGTGGTTAGCGGGGTTACAATCAGCCAAGTTATTACACCCTTATTTTACAGTCCAAAACCG
CAGGGCGGCGTGTGGGGGCTGACGCGTGCCCCCACTCCACAATTTCAAAAAAAAGAGTGGCCACTTGTCTTTGTTTATGG
GCCCCATTGGCGTGGAGCCCCGTTTAATTTTCGGGGGTGTTAGAGACAACCAGTGGAGTCCGCTGCTGTCGGCGTCCACT
CTCTTTCCCCTTGTTACAAATAGAGTGTAACAACATGGTTCACCTGTCTTGGTCCCTGCCTGGGACACATCTTAATAACC
CCAGTATCATATTGCACTAGGATTATGTGTTGCCCATAGCCATAAATTCGTGTGAGATGGACATCCAGTCTTTACGGCTT
GTCCCCACCCCATGGATTTCTATTGTTAAAGATATTCAGAATGTTTCATTCCTACACTAGTATTTATTGCCCAAGGGGTT
TGTGAGGGTTATATTGGTGTCATAGCACAATGCCACCACTGAACCCCCCGTCCAAATTTTATTCTGGGGCGTCACCTGA
AACCTTGTTTTCGAGCACCTCACATACACCTTACTGTTCACAACTCAGCAGTTATTCTATTAGCTAAACGAAGGAGAATG
AAGAAGCAGGCGAAGATTCAGGAGAGTTCACTGCCCGCTCCTTGATCTTCAGCCACTGCCCTTGTGACTAAAATGGTTCA
CTACCCTCGTGGAATCCTGACCCCATGTAAATAAAACCGTGACAGCTCATGGGGTGGGAGATATCGCTGTTCCTTAGGAC
CCTTTTACTAACCCTAATTCGATAGCATATGCTTCCCGTTGGGTAACATATGCTATTGAATTAGGGTTAGTCTGGATAGT
ATATACTACTACCCGGGAAGCATATGCTACCCGTTTAGGGTTAACAAGGGGGCCTTATAAACACTATTGCTAATGCCCTC
TTGAGGGTCCGCTTATCGGTAGCTACACAGGCCCCTCTGATTGACGTTGGTGTAGCCTCCCGTAGTCTTCCTGGGCCCCT
GGGAGGTACATGTCCC
```

```
ATGTCTGACGAGGGGCCAGGTACAGGACCTGGAAATGGCCTAGGAGAAGGAGACACATCTGGACCAGAAGGCTCCGGGCAGTGGACCTCAAAGAA
               +         +         +         +         +         +         +         +         +         +    100
TACAGACTGCTCCCCGGTCCATGTCCTTGGACCTTTACCGGATCCTCTTCCTCTGTGTAGACCTGGTCTTCCGAGGCCGCCGTCACCTGGAGTTTCTT
 M   S   D   E   G   P   G   T   G   P   G   N   G   L   G   E   K   G   D   T   S   G   P   E   G   S   G   P   Q   R

GAGGGGGTGATAACCATGGACGAGGAAGAGAACGGGCCCCGGGCGCTCAGGATCAGGGCCCGCCGAGTCCTAGTCCCGGTTCTGTATC
               +         +         +         +         +         +         +         +         +         +    200
CTCCCCCACTATTGGTACCTGCTCCTTCTCTTGCCCCGGGGGCCCGCGAGTCCTAGGTCCGGGCGGCTCAGGATCAGGGCCAAGACATAG
 R   G   G   D   N   H   G   R   G   R   G   R   G   R   G   R   P   G   A   P   G   G   S   G   P   R   H   R

AGATGGTGTCCGAGACCCAAAAACGTCCAAGTTGCATTGGCTGCAAGGGACCACCGGTGGAACAGGAGCAGGGGAGGGCAGGAGCA
               +         +         +         +         +         +         +         +         +         +    300
TCTACCACAGGCCTCTGGGGTTTTGCAGGTTCAACGACGTAAACCGACGTTTCCCTGGGTGCCACCTTGTCCTCGTCTCCCCGTCCTCGT
 D   G   V   R   R   P   Q   K   R   P   S   C   I   G   C   K   G   T   H   G   G   T   G   A   G   A   G   G   A   G   A

GGAGGGGCAGGAGCAGGGGCAGGAGCAGGAGGGGCAGGAGCAGGGGCAGGAGCAGGAGGGGCAGGAGCAGGGGCAGGAGCAGGAG
               +         +         +         +         +         +         +         +         +         +    400
CCTCCCCGTCCTCGTCCCCGTCCTCGTCCTCCCCGTCCTCGTCCCCGTCCTCGTCCTCCCCGTCCTCGTCCCCGTCCTCGTCCTC
 G   G   A   G   G   G   A   G   G   A   G   G   G   A   G   G   A   G   G   G   A   G   G   A   G

GAGGGGCAGGAGCAGGGGCAGGAGCAGGAGGGGCAGGAGCAGGGGCAGGAGCAGGAGGGGCAGGAGGGGCAGG
               +         +         +         +         +         +         +         +         +         +    500
CTCCCCGTCCTCGTCCCCGTCCTCGTCCTCCCCGTCCTCGTCCCCGTCCTCGTCCTCCCCGTCCTCCCCGTCC
 G   G   A   G   G   G   A   G   G   A   G   G   G   A   G   G   A   G   G   G   A   G   G   G

GAGGGGCAGGAGCAGGGGCAGGAGCAGGAGGGGCAGGAGGGGCAGGAGGGGCAGGAGGGGCAGGAGGGGAGGAG
               +         +         +         +         +         +         +         +         +
CTCCCCGTCCTCGTCCCCGTCCTCGTCCTCCCCGTCCTCCCCGTCCTCCCCGTCCTCCCCGTCCTCCCCTCCTC
 G   G   A   G   G   A   G   G   G   A   G   G   A   G   G   G   A   G   G   A   G   G   G   A   G   G   A   G

```
    B
    |
    GTGGAGGCCCGGGGGTCGAGGAGTAGTGGAGGCCGCCCGGGTAGAGGAGGACGTGAAAGAGCCAGGGGGAAGTCGTGA
                                                                                    1100
    CACCTCCGGCCCCAGCTCCTCCATCACCTCCGGGCCCCCATCTCCTGCACTTTCTCGTCCCCCTTCAGCACT
    S  G  G  R  G  G  S  G  R  G  G  S  G  R  R  G  R  G  R  E  R  A  R  G  G  S  R  E

AAGAGCCAGGGGAGAGGTCGTGGAGAAAAGAGGCCCAGTAGTCAGTCATCATCATCCGGGTCTCCACCGGCAGCCCCTCCA
                                                                                    1200
    TTCTCGGTCCCCTCTCCAGCACCTGCACCTCTTTTCTCCGGGTCATCAGTCAGTAGTAGCCCAGATGGCGTCCGGGGAGGT
    R  A  R  G  R  G  R  G  R  G  E  K  R  P  S  P  S  S  Q  S  S  S  S  G  S  P  R  R  P  P  P

GGTAGAAGGCCATTTTTCCACCCTGTAGGGGAAGCCTAATATTTTGAATACCACCAAGAAGTGGCCCAGATGTGAGCCTGACGTGCCCGGAGCGA
                                                                                    1300
    CCATCTTCCGGTAAAAAGGTGGACATCCCCTTCGGCTAATAAAACTTATGGTGGTTCTTCCACCGGGTCTACCACTCGGACTGCACGGGGCCCTCGCT
    G  R  R  P  F  F  H  P  V  G  E  A  D  Y  F  E  Y  H  Q  E  G  G  P  D  G  E  P  D  V  P  P  G  A

TAGAGCCAGGGCCCCCGCCAGATGACCCAGGAGAAGGCCTCTTCCGGGTCCTCGTGACCTGGGGCCCCAGTGCGTTCGTTCCCGCGTTTTTTCCTCCCACCAAACCTTT
                                                                                    1400
    ATCTCGGTCCCGGGGCGTCTACTGGGTCTACTGGGTCCTCTTCCGGAGAAGGCCAGGAGCACTGGACCCCGGGTCACGCAAGCAGGCGCAAAAAAGGAGGGTGGTTTGGAAA
    I  E  Q  G  P  A  D  D  P  G  E  G  P  S  T  G  P  R  G  Q  G  D  G  G  R  R  K  K  G  G  W  F  G  K

GCATCGTGGTCAAGGAGGTTCCAACCCGAAATTTGAGAACATTGAGGAGTCTCTGGCTAGGAGTCACGTAGAAAGGACTACCGACGAA
                                                                                    1500
    CGTAGCACCAGTTCCTCCAAGGTTGGCTTTAAACGTCTTCCAAATTCTGTAACGTCTTCCAAATTCTGAGAGGACCGATCCTCAGTGCATCTTTCTGATGGCTGCTT
    H  R  G  Q  G  G  S  N  P  K  F  E  N  I  A  E  G  L  R  A  L  L  A  R  S  H  V  E  R  T  T  D  E
    |
    C
```

FIG. 2 (Cont.)

```
C
GGAACTTGGGTCGCCGGTGTGTTCGTATATGGAGGTAGTAAGACCTCCCTTACAACCTAAGGCGAGGAACTGCCCTTGTATTCCACAATGTCTTA
                                                                                              1600
 G  T  W  V  A  G  V  F  V  Y  G  G  S  K  T  S  L  Y  N  L  R  R  G  T  A  L  A  I  P  Q  C  R  L

CCTTGAAACCCAGCGGCCACACAAGCATATACCTCCATCATTCTGGAGGGAAATGTTGGATTCCGCTCCTTGACGGGAACGATAAGGTGTTACAGCAGAAT
                                                                                              1700
                  G  V  F  V  Y  G  G  S  K  T  S  L  Y  N  L  R  R  G  T  A  L  A  I  P  Q  C  R  L

CACCATTGAGTCGTCTCCCCTTTGGAATGCCCCTGGACCCGGCCCCACAACCTGCCGCTAAGGGAGTCCATTGTCTGTTATTTCATGGTCTTTTTACA
                                                                                              1700
 T  P  L  S  R  L  P  F  G  M  A  P  G  P  G  P  Q  P  G  P  L  R  E  S  I  V  C  Y  F  M  V  F  L  Q

GTGGTAACTCAGCAGAGAGGGAAACCTTACCGGGACCTGTTGACCGGGCCGATTCCCTCAGGTAACACAGACAATAAAGTACCAGAAAAATGT
                                                                                              1800
 T  P  L  S  R  L  P  F  G  M  A  P  G  P  G  P  Q  P  G  P  L  R  E  S  I  V  C  Y  F  M  V  F  L  Q

AACTCATATATTTGCTGAGGTTTTGAAGGATGCGATTAAGGACCTTGTTATGACAAAGCCCGCTCCTACCTGCAATATCAGGGTGACTGTGTGCAGCTTT
                                                                                              1800
                                                                                    V  C  S  F

TTGAGTATATAAACGACTCCAAAACTTCCTACGCTAATTCCTGAACACATACTGTTTCGGGCGGAGATGGACGTTATAGTCCCACTGACACACGTCGAAA
                                                                                              1800
 T  H  I  F  A  E  V  L  K  D  A  I  K  D  L  V  M  T  K  P  A  P  T  C  N  I  R  V  T  V  C  S  F

GACGATGGAGTAGATTTGCTCCCTGGTTTCCACCTATGGTGGAAGGGCTGCCGCGGAGGGTGATGACGGAGATGACGGAGATGAAGGAGGTGATGGAG
                                                                                              1900
 D  D  G  V  D  L  P  P  W  F  P  P  M  V  E  G  A  A  A  E  G  D  D  G  D  D  D  G  D  E  G  G  D  G

CTGCTACCTCATCTAAACGGAGGACCAAAGGTGGATACCACCTTCCCCGACGGCCCTCCCACTACTGCCTCCTCCACTACCTC
 D  D  G  V  D  L  P  P  W  F  P  P  M  V  E  G  A  A  A  E  G  D  D  G  D  D  D  G  D  E  G  G  D  G

ATGAGGGTGAGGAAGGGCAGGAGTGA   1926
TACTCCCACTCCTTCCCGTCCTCACT
 Q  E  E  G  Q  E
```

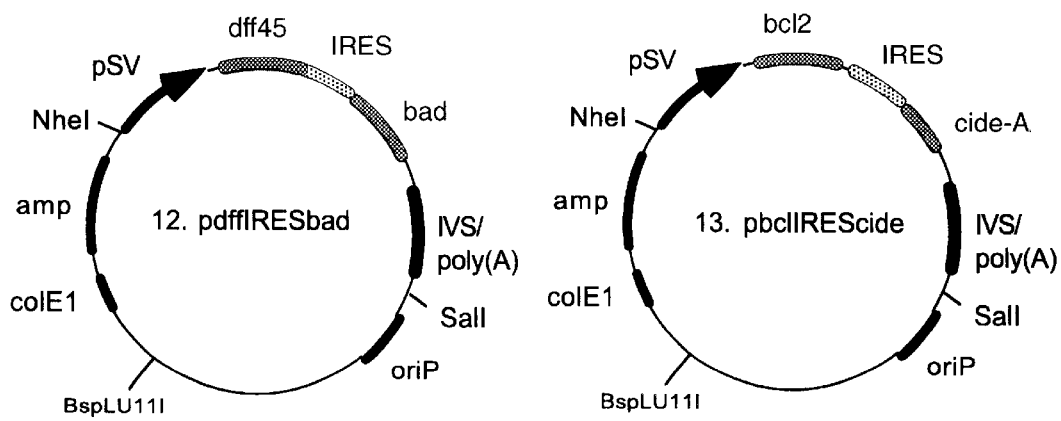
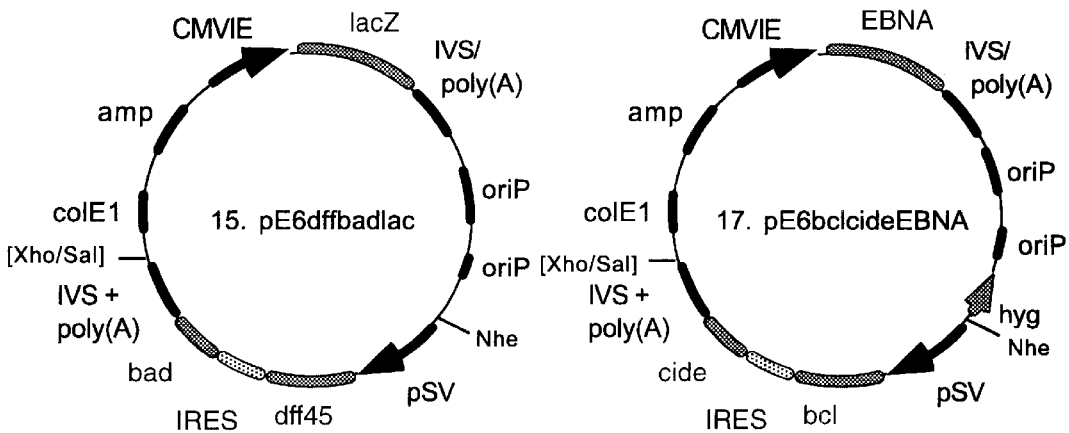
FIG. 3D

METHOD FOR MAINTENANCE AND SELECTION OF EPISOMES

FIELD OF THE INVENTION

The present invention relates to methods which allow for the stable maintenance and selection of at least one episome in eukaryotic cells. The invention can be used to maintain and select episomes in cultured cells as well as in cells that are the subject of gene therapy without the need for exogenous selection factors, such as antibiotics.

BACKGROUND OF THE INVENTION

In the field of molecular biology it is often desirable to express exogenous proteins in eukaryotic cells. This can be achieved through the stable maintenance of exogenous DNA encoding the proteins of interest in the desired cells. One method for producing stably transfected eukaryotic cells which express a gene of interest requires integration of multiple genes into one or more chromosomal loci. However, integration of exogenous genes into chromosomes is unpredictable and it is normally necessary to screen many clonal cell populations to obtain a cell line in which all of the desired genes are expressed at an appropriate level. This process is time consuming.

Recently, non-integrating, autonomously replicating episomal vectors have been used to circumvent many of these difficulties. The Epstein Barr Virus (EBV) Nuclear Antigen 1 protein (EBNA 1) has been used to stably maintain plasmids containing the EBV origin of replication (oriP) in primate cells (Reisman, D. et al, *Mol. Cell. Biol.* 5: 1822–1832, 1985; Yates, J. L. et al., *Nature* 313:812–815, 1985). EBNA1 is the only protein that is required in primate and canine cells to maintain plasmids that contain an EBV origin of replication in an episomal state.

Transfection of cell lines that already express EBNA1 can be extremely advantageous, as the ability of such cells to stably maintain episomal constructs can be enhanced by several orders of magnitude and stable cell lines can be generated in as little as two to three weeks (Horlick et al., *Prot. Exp. And Purific.* 9:301–308, 1997). These methods, however, require the additional step of producing a cell line which constitutively expresses EBNA1 from an integrated gene. Alternately, a single plasmid which contains the EBV oriP and the EBNA1 gene and the gene or genes encoding a protein of interest can be used to transfect cells. For this technique to succeed, all of these genes must be driven by strong promoters, which can cause "promoter occlusion" (Greger, I. H. et al., *Nuc. Acid Res.* 26(5) 1214–1301, 1998; Kadesch, T. et al., *Mol. Cell. Biol.* 6(7): 2593–2601, 1986).

One solution to the problem of promoter occlusion, described in U.S. patent application Ser. No. 09/130,114, filed on Aug. 6, 1998, uses two episomes, one of which contains an EBNA1-encoding gene and the other of which contains a gene encoding a protein of interest. In this approach, the episome containing the gene which encodes the protein of interest is maintained as an autonomously replicating plasmid in the presence of the episome containing the EBNA1 gene.

In all of the methods described above, however, conventional selection markers are employed in order to select for cells that have been successfully transfected with an episome encoding the desired sequences. Such selection normally involves exposing transfected cells to antibiotics or other substances that initiate the relevant selection process. Where transfected genes integrate into the cellular chromosome, a single marker is required. Where the continued maintenance of multiple episomes is desired, each episome generally carries its own resistance marker. It would be advantageous to select and maintain transfected cells, both in conventional cell-culture and in gene therapy methods, without the need for an exogenous selection agent, such as an antibiotic. It would also be advantageous to do so quickly, reliably, and without positional effects associated with certain prior art methods.

Accordingly, there is a need in the art for novel methods which allow for the stable maintenance of one or more episomes in eukaryotic cells. Furthermore, there is a need for methods and compositions that allow for the stable maintenance of exogenous DNA in cells of a mammalian organism, i.e., that can be used in gene therapy in vivo or ex vivo.

SUMMARY OF THE INVENTION

In one embodiment, the present invention relates to a method for transfecting eukaryotic cells with exogenous nucleic acid encoding a protein or RNA the expression of which is desired in the eukaryotic cells. According to the invention, the eukaryotic cell is transfected with the exogenous nucleic acid encoding the protein or RNA the expression of which is desired, and with nucleic acid encoding a kill antagonist protein whose expression prohibits the occurrence of cell death resulting from expression of a kill agonist protein by the cell. Successfully transfected eukaryotic cells express the exogenous nucleic acid encoding the protein or RNA the expression of which is desired, and also both the kill agonist protein and the kill antagonist protein, allowing the eukaryotic cell to live. Unsuccessfully transfected eukaryotic cells, i.e., wherein the exogenous nucleic acid encoding the desired protein or RNA is not expressed, express the kill agonist protein, but not the kill antagonist protein. Therefore, the unsuccessfully transfected eukaryotic cells do not live. Preferably, the nucleic acid encoding the protein or RNA the expression of which is desired, and the nucleic acid encoding the kill antagonist protein, are contained in an episome transfected into the cell.

The present invention also provides, in another aspect, methods for obtaining a eukaryotic cell stably transformed with at least one episome, which methods can be used in cell culture or in intact organisms. These methods are carried out by the steps of:

(a) transfecting a eukaryotic cell with:
  (i) a first episome which comprises (a) an EBV origin of replication (oriP); (b) a gene encoding a first protein whose expression results in cell death; and (c) a selectable marker for eukaryotic cells; and
  (ii) a second episome comprising (a) an EBV(oriP); and (b) a gene encoding a second protein whose expression prohibits the occurrence of cell death resulting from expression of the first protein, to produce doubly transfected cells, wherein said cells express an EBNA-1 protein, preferably from nucleic acid contained in at least one of the first and second episomes.

(b) maintaining the doubly transfected cells under conditions in which (i) the first and second proteins and the selectable marker are expressed and (ii) the selective pressure specified by the marker is maintained. Under these conditions, only cells containing both episomes live. The selectable marker on the first episome can be a conventional marker, such as DNA encoding antibiotic resistance, or can encode a second kill antagonist protein that antagonizes a second kill agonist protein expressed by the cell.

Preferably, either or both episomes additionally comprise nucleic acid that encodes a third protein whose expression is desired, in particular a protein that is not normally a selectable marker such as a therapeutic protein. Where only one of the episomes encodes an EBNA1 protein, the protein of interest is preferably expressed from the other episome.

It is also possible, according to the invention, to transfect cells with episomes that do not encode a particular protein or RNA desired to be expressed by the cells. One or both of the episomes may, for example, instead contain a nucleic acid sequence useful as a tag to identify the transfected cells. Other uses of the invention will be apparent to those skilled in this art.

In another series of embodiments, the first episome comprises (a) an EBV origin of replication and (b) a gene encoding a first protein whose expression results in cell death; the second episome comprises (a) an EBV origin of replication and (b) a gene encoding a second protein whose expression prohibits the occurrence of cell death resulting from expression of the first protein; and at least one of the episomes preferably comprises a gene encoding an EBNA1 protein. In addition, the second episome comprises a gene encoding a fourth protein whose expression results in cell death by a mechanism distinct from that of the first protein; and the first episome further comprises a gene encoding a fifth protein whose expression prohibits the occurrence of cell death which results from expression of the fourth protein. In these embodiments, no conventional selectable marker for eukaryotic cells, e.g., an antibiotic resistance marker, is required on either episome, although the invention is advantageously practiced using an additional marker that is useful for separating transfected from untransfected cells. Nevertheless, even in the absence of an external selective pressure, cells expressing only the first or second episome die, whereas cells expressing both episomes live.

In another aspect, the present invention provides a system for expressing a gene of interest in a eukaryotic cell, which comprises appropriately matched pairs of the episomes described above.

The invention allows the rapid establishment of eukaryotic cells that stably and reliably express a gene of interest, using a novel method of selection, and maintenance of that selection.

These and other aspects of the present invention will be apparent to those of ordinary skill in the art in light of the present specification, claims and drawings.

BRIEF DESCRIPTION OF THE DRAWINGS

FIG. 1 shows the nucleotide sequence of EBV oriP (SEQ ID NO: 1).

FIG. 2 shows the 1926 base pair nucleotide sequence, i.e., the coding strand (SEQ ID NO. 2) and template strand (SEQ ID NO. 4), and corresponding amino acid sequence, of EBNA 1.

FIGS. 3A, 3B, 3C, and 3D schematically depict steps employed in the construction of episomes described in the Example.

DETAILED DESCRIPTION OF THE INVENTION

All patent applications, patents and literature references cited herein are hereby incorporated by reference in their entirety.

In practicing the present invention, many conventional techniques in molecular biology, microbiology, and recombinant DNA are used. Such techniques are well known and are explained in, for example, Sambrook et al., 1989, *Molecular Cloning: A Laboratory Manual,* Second Edition, Cold Spring Harbor Laboratory Press, Col Spring Harbor, New York; *DNA Cloning: A Practical Approach,* Volumes I and II, 1985 (D. N. Glover ed.); *Oligonucleotide Synthesis,* 1984 (M. L. Gait ed.); *Nucleic Acid Hybridization,* 1985, (Hames and Higgins); *Transcription and Translation,* 1984 (Hames and Higgins eds.); *Animal Cell Culture,* 1986 (R. I. Freshney ed.); *Immobilized Cells and Enzymes,* 1986 (IRL Press); Perbas, 1984, *A Practical Guide to Molecular Cloning;* the series, *Methods in Enzymology* (Academic Press, Inc.); *Gene Transfer Vectors for Mammalian Cells,* 1987 (J. H. Miller and M. P. Calos eds., Cold Spring Harbor Laboratory); and *Methods in Enzymology* Vol. 154 and Vol. 155 (Wu and Grossman, and Wu, eds., respectively); *Current Protocols in Molecular Biology,* John Wiley & Sons, Inc. (1994), and all more recent editions of these publications The present invention provides methods and compositions that allow for the stable maintenance of one or more episomes in eukaryotic cells. The invention is particularly suitable for transfecting cells in vivo, or, alternatively, for ex vivo transfection, which can be followed by introduction of the transfected cells into an intact organism. The invention may be used for cultured cells and/or for gene therapy.

The expression of certain proteins results in cell death. Such proteins are referred to herein as kill agonists. The expression of certain other proteins prohibits the occurrence of cell death resulting from expression of the kill agonists. Such proteins are referred to herein as kill antagonists. Without wishing to be bound by any theory of the invention, it is believed that stable maintenance of an episome within a cell is achieved if (i) the cell contains an episome encoding a kill agonist that causes the cell to express the agonist at a level that, in the absence of the antagonist, would result in cell death and, (ii) at the same time, the cell expresses an appropriate amount of a cognate kill antagonist to counteract the effect of the agonist. Preferably, the kill antagonist is encoded by a second episome. The invention thus, in a preferred embodiment, provides multiple-episome systems and methods that allow the stable maintenance of episomes in eukaryotic cells.

Figure 3A:
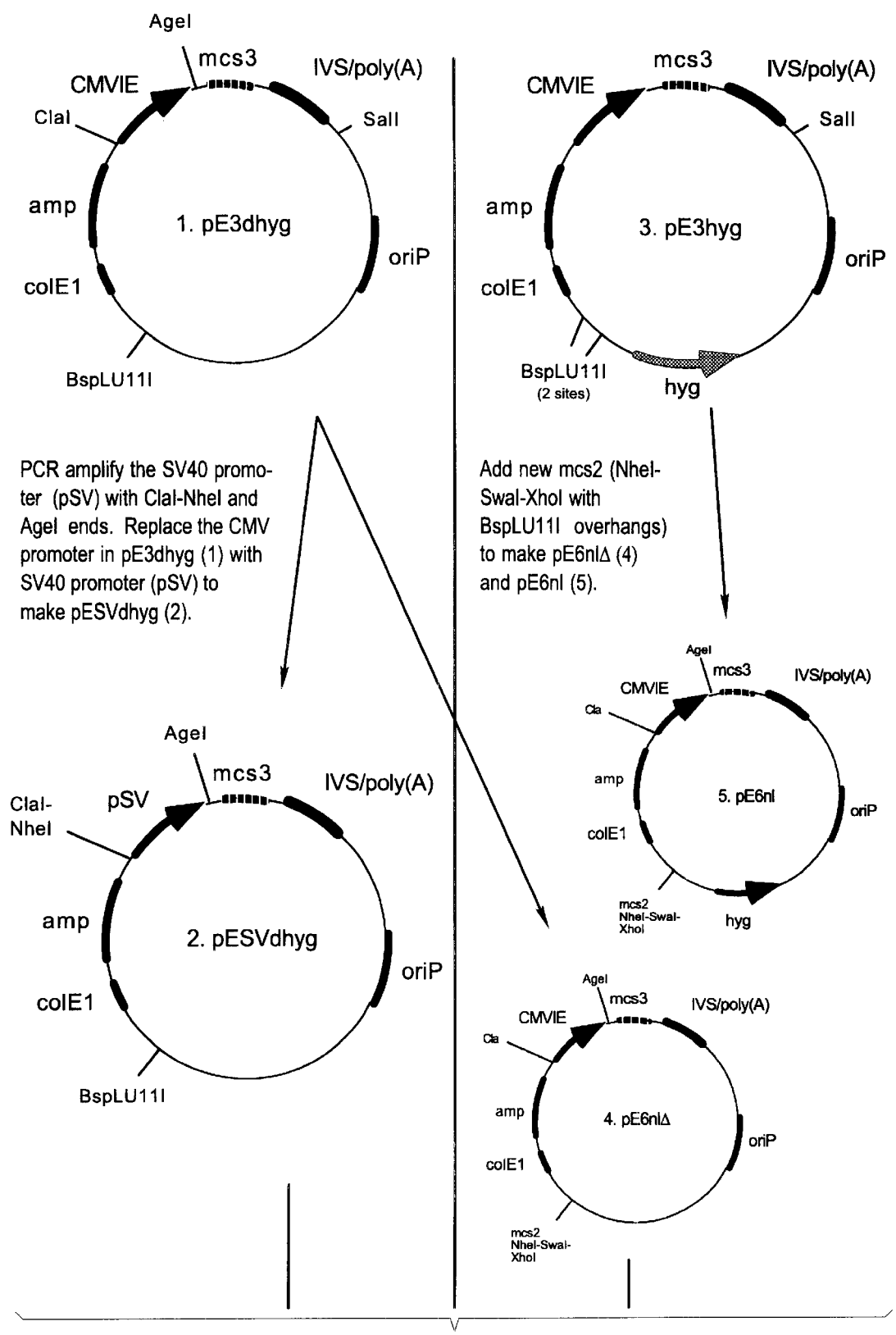
Figure 3B:
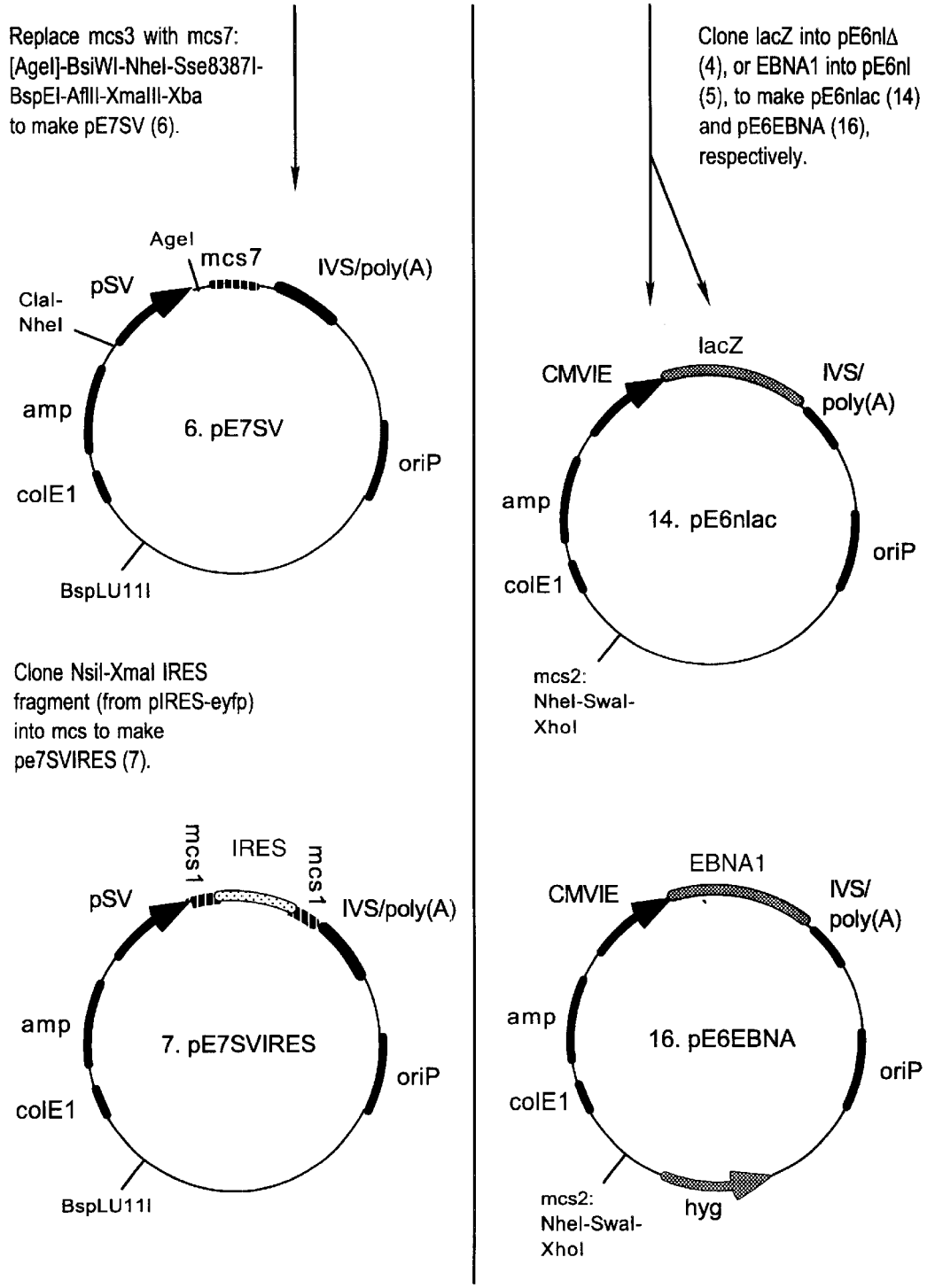
Figure 3C:
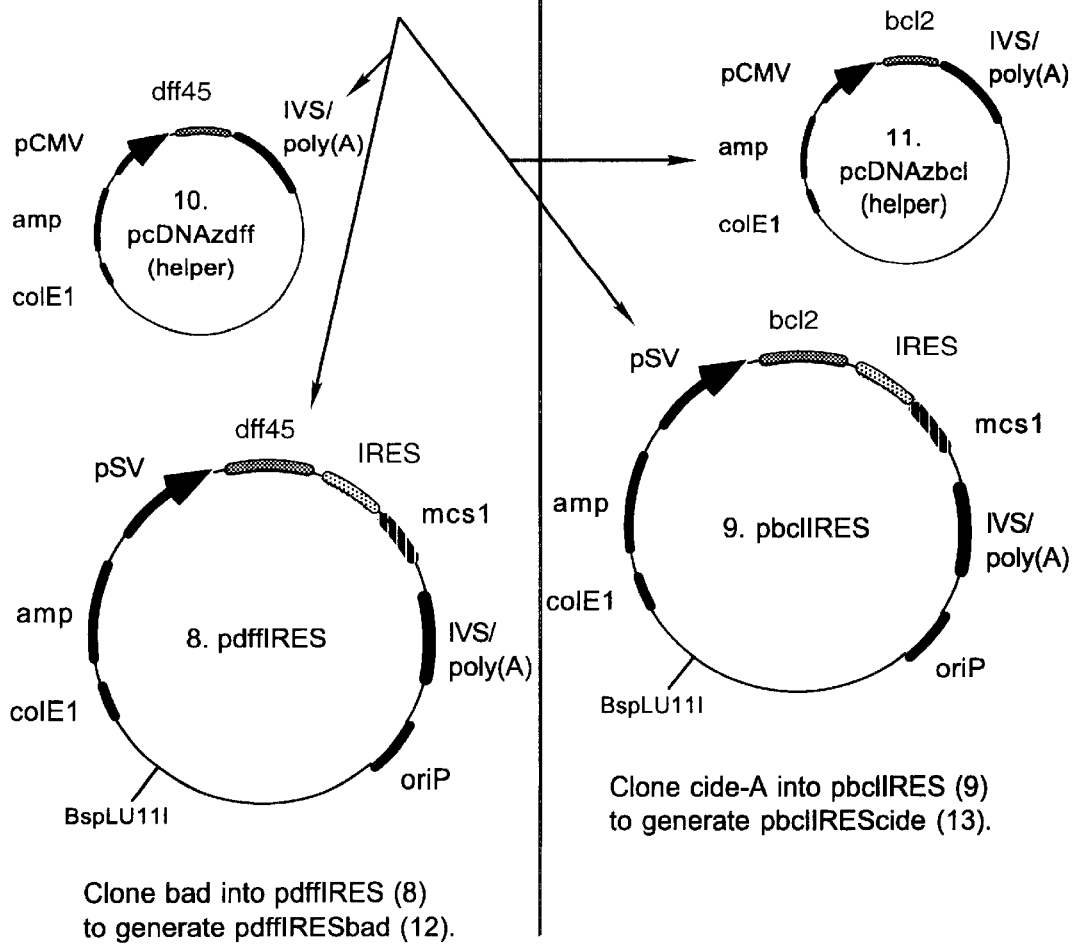
Figure 4A:
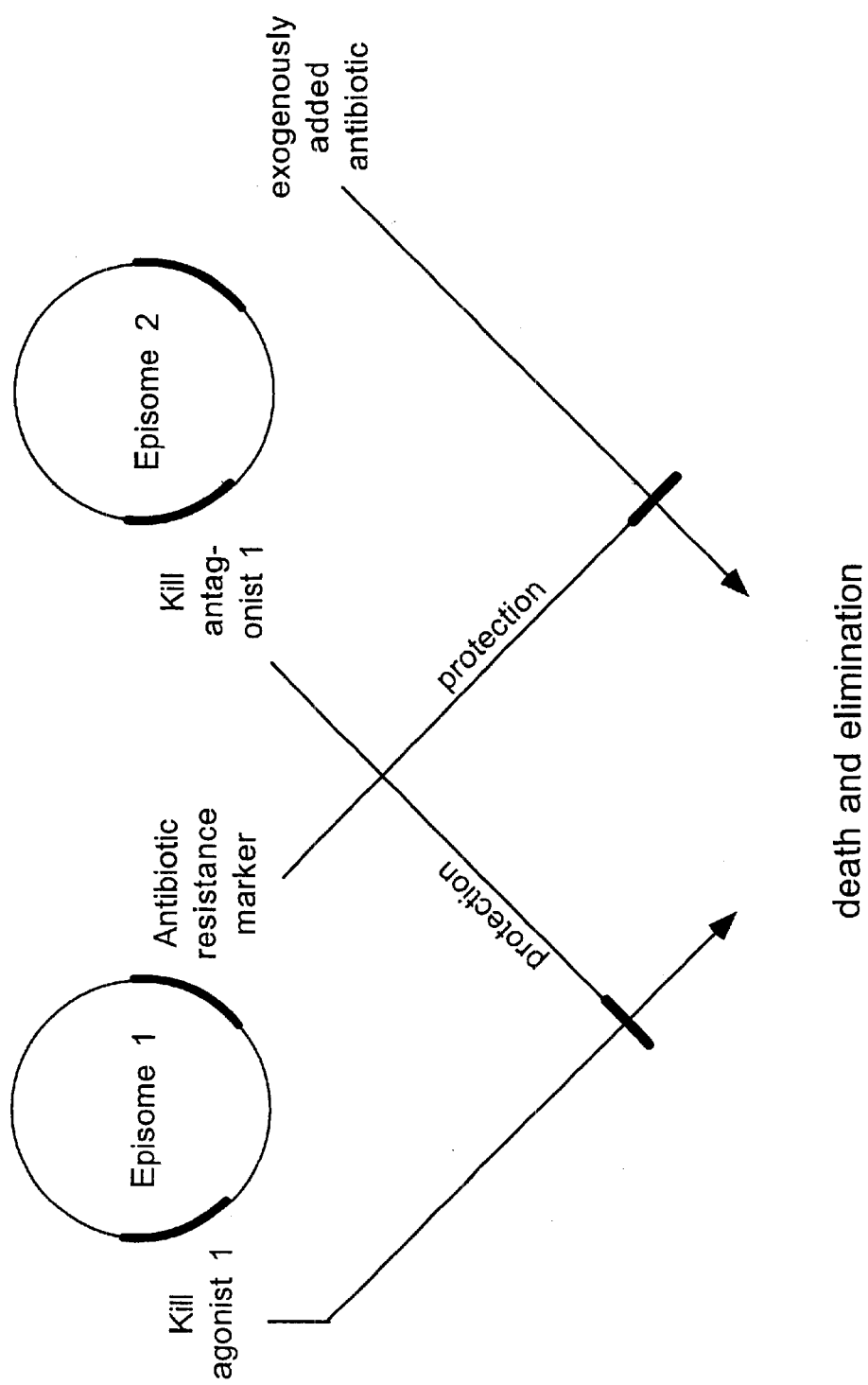
FIGS. 4A, 4B, and 4C schematically depict methods of transfection of cells according to the invention. In the method depicted in FIG. 4A, two episomes are employed to transfect eukaryotic cells, one episome encoding a kill agonist and a non-kill antagonist resistance marker (in particular an antibiotic resistance marker), and the other episome encoding a kill antagonist. In the method depicted in FIG. 4B, two episomes are used to transfect eukaryotic cells, one episome encoding kill agonist 1 and kill antagonist 2, and the second episome encoding kill agonist 2 and kill antagonist 1. In the method depicted in FIG. 4C, three episomes are employed to transfect a eukaryotic cell, each episome encoding a kill agonist and kill antagonist, with a total of three kill agonist/antagonist pairs employed.

FIG. 4A schematically depicts transfection according to the invention in which episome 1 encoding kill agonist 1 and an antibiotic resistance marker is co-transfected with episome 2 encoding kill antagonist 1. Where cells are effectively transfected with both episomes, the cells are protected against cell death resulting from expression of kill agonist 1. The antibiotic resistance marker allows elimination of cells that have only been transfected with episome 2, or which have been transfected with neither episome.

Figure 4B:
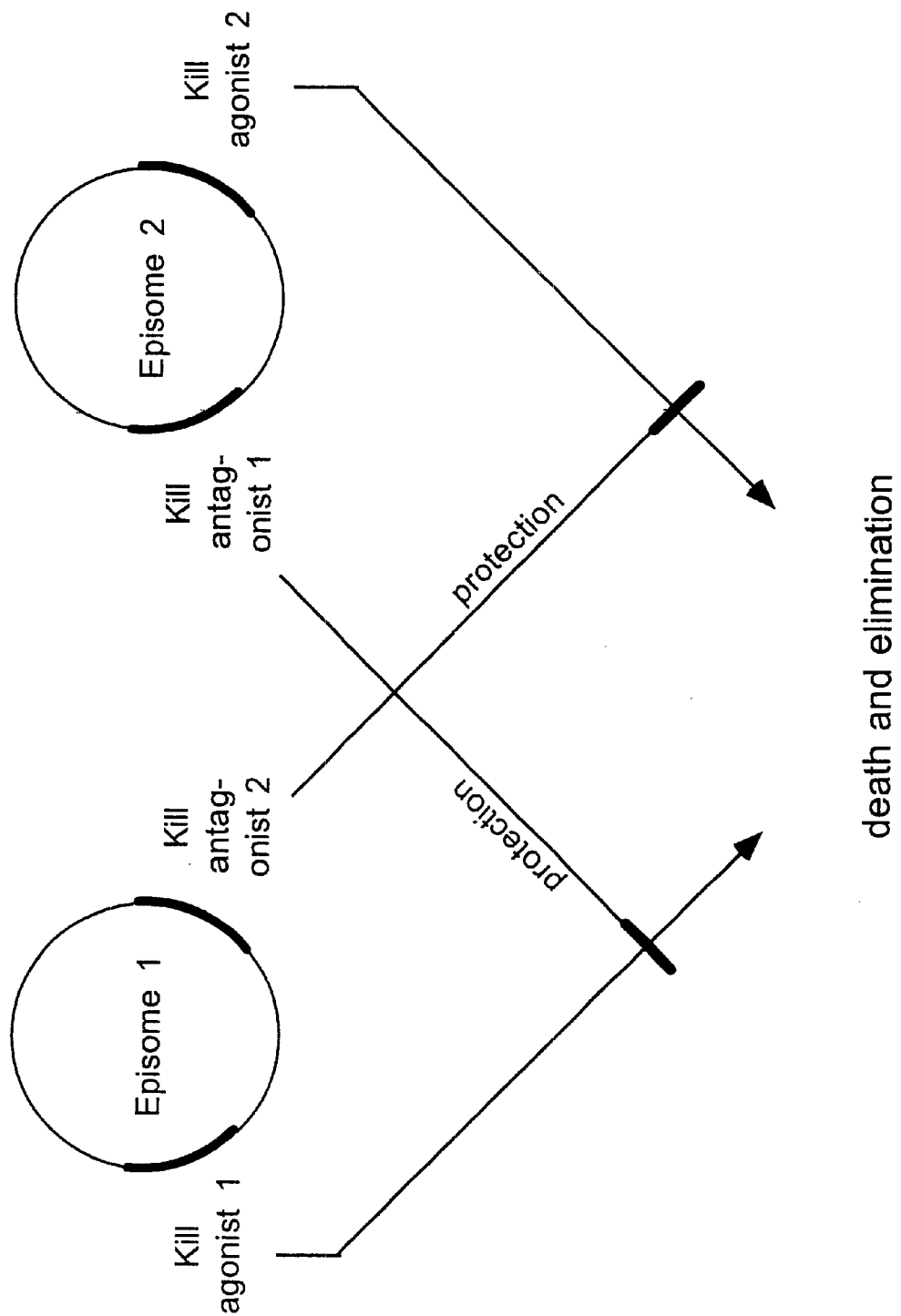

Another embodiment of the invention is depicted in FIG. 4B in which cells are co-transfected with episome 1, encoding kill agonist 1 and kill antagonist 2, and with episome 2 encoding kill antagonist 1 and kill agonist 2. Only cells that are successfully transfected with both episomes are protected against cell death resulting from expression of either of the kill agonists. In this embodiment, a non-kill antagonist selectable marker for eukaryotic cells (e.g., an antibiotic resistance marker) is not necessary, but may nevertheless be advantageously included in either episome to eliminate cells that have not been transfected with either episome.

Figure 4C:
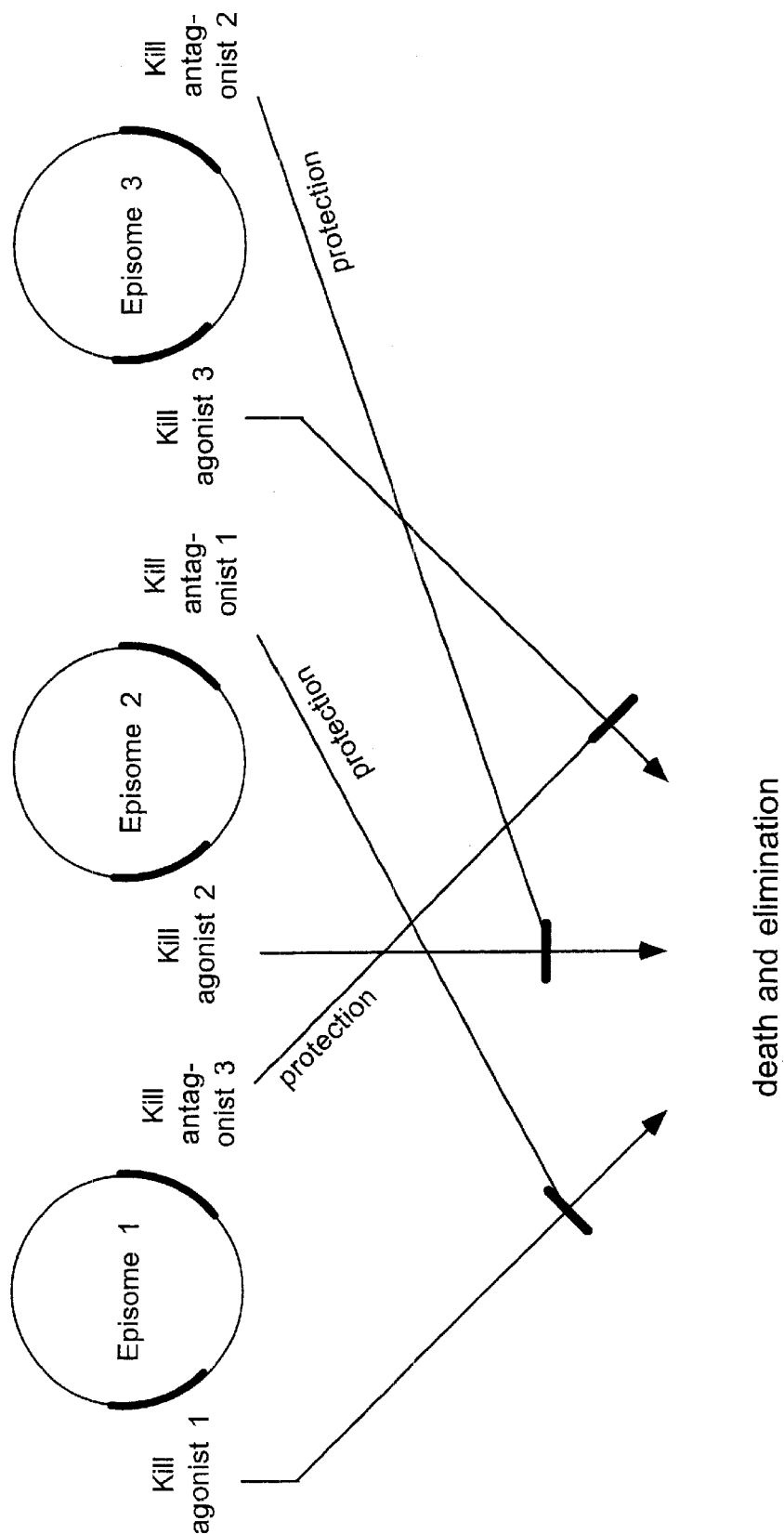

A further embodiment of the invention is depicted in FIG. 4C in which three episomes are transfected into the eukaryotic cells. Episome 1 encodes kill agonist 1 and kill agonist 3; episome 2 encodes kill agonist 2 and kill antagonist 1; and episome 3 encodes kill agonist 3 and kill antagonist 2. Cells that are transfected with all three episomes are protected from cell death arising from partial transfection, i.e., from transfection with only 1 or 2 of the episomes, since cells that are only partly transfected will express a kill agonist without its cognate kill antagonist.

In a preferred embodiment the kill agonist is a protein which causes apoptosis (i.e. programmed cell death), and the kill antagonist is a protein which counteracts apoptosis caused by the kill agonist. Thus, expression of both the protein causing apoptosis and the protein which counteracts apoptosis results in cell survival according to the invention, and thus selection of cells that also preferably express a protein or RNA of interest. Such apoptotic proteins and counteracting proteins, and the genes expressing them, are known to those skilled in this art. Some non-limiting examples are listed below in Table1, which shows the interactions of certain apoptotic agonists and antagonists with each other.

TABLE 1

| Kill antagonist | Kill agonist Bax | Kill agonist Bak | Kill agonist Bad |
|---|---|---|---|
| Bcl2 | ++ | U | + |
| Bcl-$X_L$ | ++ | + | + |
| Bcl-$X_S$ | – | + | – |
| adenoE1b | ++ | U | – |
| A1 | ++ | + | – |
| Mcl-1 | + | ++ | – |

U = unknown interaction
++ = strong interaction
+ = intermediate interaction
– = very weak or no interaction According to the invention, a kill agonist is preferably paired with a kill antagonist with which it strongly interacts. For example, the kill agonist Bak is preferably paired with the Mcl-1 kill antagonist in order to promote survival of cells that are successfully transfected with both proteins. Where two pairs of kill agonists and antagonists are employed in the practice of the invention, the pairs preferably do not substantially interact with each other.

Apoptotic kill antagonists and agonists listed in Table1 are described in the following publications: Chen et al., *J. Biol. Chem.* 271: 24221–24225, 1996; Farrow et al., *Nature* 374: 731–734, 1995; Farrow and Brown, *Curr. Opin. Genet. Dev.* 6:45–49, 1995; Sedlak et al., *PNAS* 92: 7834–7838, 1995; Kitada et al., *Am. J. Pathol.* 152:51–61, 1998, *Proc. Natl. Acad. Sci. U.S.A.* 83:5214–5218, 1986; and Yang and Korsmeyer, *Blood* 88: 386–401, 1995.

Use of other apoptotic and anti-apoptotic proteins is encompassed by the invention. For example, the kill agonist adenovirus E1a can be paired with the kill antagonist adenovirus E1b 19k protein. These proteins are described in Rao et al., *Oncogene* 15: 1587–1597, 1997. Similarly, the kill agonist ICE (interleukin-1β converting enzyme, a known cysteine protease) can be paired with the kill antagonist CrmA. These proteins are described in Antoku et al., *Leukemia* 11:1665–1672, 1997.

In one embodiment, an apoptotic/anti-apoptotic pair of proteins is used to practice the present invention that does not substantially interact with bax/bcl family members. These pairs of kill agonists and agonists can be employed in the embodiment of the invention where one pair of kill agonists/antagonists is used, but are particularly suitable for use where two pairs are employed. For example, they can be used in combination with a pair from Table 1, since the pairs do not interact adversely with each other.

For example, the kill agonist DNA fragmentation factor (dff) 40 kDa subunit pairs with the kill antagonist+dff 45 kDa subunit (dff45), as described in Liu et al., *Proc. Natl. Acad. Sci.* USA 95:8461–8466, 1998. dff subunits are also described in Sabol et al. *Biochem. Biophys. Res. Commun.* 253:151–8, 1998; and Liu et al., *Cell* 89:175–84, 1997. These proteins do not substantially interact with the proteins listed in Table 1, and can be advantageously employed as a second pair of kill agonist and antagonist proteins in the invention.

Alternately, the kill agonist cide-a (cell death activator) is paired with the kill antagonist dff 45 kDa subunit; or the kill agonist cide-b is paired with the kill antagonist dff 45 kDa subunit. These proteins are described in Inohara et al. *EMBO. J* 17:2526–2533, 1998. Alternately, the kill agonist cad (caspase activated DNAse) can be paired with the kill antagonist icad (inhibitor of cad). These are known murine homologues for dff-40 and dff-45, respectively. The following references describe the cad and icad proteins: Sakahira et al. *Nature* 391:96–99, 1998.; and Enari et al., *Nature* 391:43–50, 1998, published erratum in *Nature* 393:396, 1998. The pairing of cide-a and dff 45 is believed to be particularly advantageous in practicing the invention.

Sequences for these factors are known, and available to those skilled in this art. For example, the sequence for human DNA fragmentation factor 40 kDa subunit (dff40), is found at Genbank accession number AF064019 and for human DNA fragmentation factor 45 (dff45) at accession number U91985.

Other examples of cognate pairs of apoptotic and anti-apoptotic proteins that do not substantially interact with other cognate pairs will be apparent to those of ordinary skill in this art.

The nucleotide and protein sequences of the apoptotic and anti-apoptotic genes described above, are available to those practicing in this field. For example, relevant sequences can be obtained via GenBank, and searching via PubMed, and Entrez. Genes encoding these proteins can be synthesized, or PCR amplified from an appropriate tissue source.

Nonlimiting examples of sequences that can be used to practice the invention are listed below:
Human A1 protein—accession number U29680.
Homo sapiens bcl-xL/bcl-2 associated death promoter (bad)—accession number AF031523.
Human Bak protein—accession number U23765.
Human Bak—accession number U19599
Rattus norvegicus Bcl-2 associated death promoter bad (bad)—accession number AF031227.
Rattus norvegicus programmed cell death repressor bcl-x long—accession number U34963.
Mus musculus bcl-x short—accession number U10100.
Homo sapiens cell death activator cide a (cide-a)—accession number AF041378.

Mus musculus cell death activator cide b (cide-b)—accession number AF041377.

While the pairs above are suitable, any functional pair of kill agonists and antagonists may be used to practice the invention. The pairs are generally appropriate where (i) cells expressing the agonist, in the absence of antagonist, die and (ii) expression of the antagonist in agonist-expressing cells allows the cells to survive.

For example, in an alternate preferred embodiment the kill agonist is a neutralizing intrabody, that is, an intracellular, non-secreted antibody, such as a single chain Fv antibody, that is directed against a critical cell component. Non-limiting examples of such neutralizing intrabodies include those that are directed against enzymes involved in the nucleotide biosynthetic pathway, such as dihydrofolate reductase, against enzymes involved in cellular respiration such as Na, K-ATPase, and against cell cycle regulating enzymes such as cdc42, and EF2. The kill antagonist of this embodiment can be a functional form of the cellular target having an altered amino acid sequence that is not recognized by the intrabody. For example, the kill antagonist can be a homologue of the target from a different species, or a mutated version of the target, having an altered epitope wherein the homologue or mutated version functions for its intended purpose but is not recognized by the neutralizing intrabody. (Chen, S. Y. et al., *Hum Gene Ther.* 5(5): 595–601, 1994).

In another alternate embodiment, the kill agonist is a toxin that specifically inactivates a cellular protein. For example, the kill agonist can be a polypeptide toxin, such as a known toxin derived from bacteria. The kill antagonist of this embodiment is a substance that confers resistance to the toxin. Non-limiting examples of such toxin/resistance-to-toxin pairs include the S1 subunit of Pertussis toxin (Ptx) and mutant Gi alpha, respectively (Wise et al., *Biochem J* 321: 721–728, 1997) and fragment A of Diptheria toxin (DTX) and mutant elongation factor 2 (EF2), respectively (Floey et al., *J Biol. Chem.* 270: 23218–23225, 1995).

As used herein, the term "episome" is intended to refer to an extrachromosomal DNA moiety or plasmid that can replicate autonomously in a host cell when physically separated from the chromosomal DNA of the host cell. Such episomes are well-known in this art. An episome is considered to be "stably" maintained in a cell as a result of practice of the invention when any of the following occurs: (i) the episome is maintained in the cell for at least about one month, preferably two months, following initial introduction of the episome into the cell, or (ii) the episome is maintained in the host cell and its daughter cells for a period corresponding to at least about 10, and preferably about 20, cell doublings. Most preferably, the episome is maintained for up to and exceeding three months, or in another embodiment for a period corresponding to about 50 or more cell doublings, following initial transfection. The stability of episomal maintenance may be determined by detection of (i) extrachromosomal plasmid DNA as measured for example by genomic Southern Blot or $^3$H incorporation, 5-bromo-2'-deoxyuridine, and/or (ii) expression of any gene encoded by the episome, as reflected in steady-state mRNA levels or in the protein product. A gene encoding a kill agonist or antagonist conventionally comprises, in a 5'-to-3' direction, (i) a DNA sequence comprising a promoter operably linked to (ii) a DNA sequence encoding the agonist or antagonist protein linked to (iii) a sequence comprising a transcription termination/polyadenylation sequence, such that introduction of the episome into the desired target cell results in expression of the agonist or antagonist protein at an appropriate level. In the case of kill agonists, one appropriate expression level is the lowest level that results in cell killing. For kill antagonists, one appropriate expression level is the lowest level that antagonizes the cell killing effect of the cognate agonist. Other levels of expression, however, are encompassed by the invention, and determination of expression levels is not required to obtain a functional kill agonist/antagonist pair. Nevertheless, in one embodiment, each episome employed in the invention contains expression cassettes that are adapted to express more of the antagonist than the cognate agonist. In the embodiment where one episome encodes agonist 1/antagonist 2 (i.e., the agonist of one pair and the antagonist of another) and the other episome encodes agonist 2/antagonist 1 (i.e., the cognate agonist/antagonist pair), this can be accomplished by having the agonist and antagonist expressed by the same promoter in each episome, but placing the sequence encoding the antagonist upstream of the sequence encoding the agonist. An IRES (internal ribosome entry site) sequence is advantageously included between the antagonist and agonist encoding sequences. IRES sequences are described in the following references: Rees et al., *MB Biotecniques* 20:102–110, 1996; Jang et al., *Genes Dev.* 4:1560–72, 1990; and Gurtu et al., *Biochem. Biophys. Res. Commun.* 229:295–89, 1996. An IRES sequence can be obtained, e.g., from Clontech, Palo Alto, Calif. (vector pIREShyg). Appropriate expression levels of kill agonists and antagonists can also be achieved by the use of heterologous promoters.

If desired, appropriate expression levels of kill agonists and antagonists can be easily determined using methods well-known in the art. For example, an appropriate expression level for a kill agonist may be determined by (i) transfecting cell cultures with an episome containing nucleic acid encoding the agonist operably linked to an inducible promoter; (ii) inducing different levels of expression of the promoter; and (iii) determining the minimum expression level that results in uniform cell killing. Once this level has been established, the cells can be transfected with a second episome encoding the cognate kill antagonist, and, using the same approach, the minimum expression level of the antagonist that results in cell survival in the doubly-transformed cells determined. Alternatively, different promoters may be tested for their ability to support an appropriate level of expression, in the presence, or even in absence, of exogenous inducers.

Each episome used in practicing the present invention preferably also comprises (i) a sequence that promotes autonomous replication of the episome in eukaryotic cells; (ii) a sequence that promotes nuclear retention of the episome; (iii) a sequence comprising a bacterial origin of replication; and (iv) a sequence comprising a selectable marker gene for bacterial cells.

At least one of any pair of episomes preferably comprises a gene encoding an EBV EBNA1 antigen driven by a strong promoter as defined below, which interacts with an EBV oriP sequence to promote replication. It is, however, also possible to transfect episomes according to the invention into cells that constitutively express an EBNA1 antigen, or another antigen that promotes nuclear retention of the episome.

For example, instead of employing an EBNA1 antigen and EBV origin of replication, it is possible to employ bovine papilloma virus (BVP) E1 and E2 antigens in combination with the BVP origin of replication. The E1 antigen is a helicase required for initation of replication and elongation while the E2 antigen is a transcription factor that assists binding of the E1 antigen to the origin of replication.

M. P. Calos, *PNAS*, 95:4084–4085, 1998. These antigens promote nuclear retention of the episome in cells that are competent for appropriate transfection, such as, e.g., murine cells.

Preferably, one or both of the episomes of the invention also comprise a gene encoding an RNA, which, most preferably, encodes a protein of interest. These components are further described below.

Eukaryotic components: Any suitable EBV origin of replication DNA sequence can be employed in the episomes used in the present invention. An example of a suitable EBV origin of replication sequence (oriP) is disclosed in GenBank locus "GB:EBV". The oriP region spans the sequence from nucleotide 7337 to the natural HpaI restriction site at nucleotide 9137 in this GenBank sequence. FIG. 1 shows the nucleotide sequence of a suitable EBV oriP, contained within nucleotides 8146–9946 of pCEP4 (commercially available from Invitrogen, Carlsbad, Calif.). This sequence includes the family of repeats (first underlined region in FIG. 1) and the region of dyad symmetry (second underlined region in FIG. 1), which are required for oriP function. EBV oriP sequences that can be used in the invention include those containing modifications from naturally occurring sequences, such as those containing deletions, insertions, substitutions and duplications, of native sequences. Such derivative sequences are obtainable, for example, by maintaining the known regions described above that are required for oriP function. Also, conservative substitutions are well known and available to those in the art. The oriP sequence employed is one that functions effectively in the host cell to direct the replication of the episome in which the oriP sequence is found in the presence of a sufficiently high amount of an EBNA 1 protein.

DNA encoding any suitable EBNA 1 protein can be expressed by the transfected cells. An example of EBNA 1-encoding DNA is shown in FIG. 2. EBNA 1-encoding DNA is commercially available from Invitrogen, and is contained in several of its EBV series plasmids, including pCMVEBNA, catalog number V200-10. DNA sequences encoding truncated versions of EBNA 1 (including, e.g., those commercially available from Invitrogen such as pREP7 or pREP10 under catalog numbers V007-50 and V010-50, respectively) are well known and can be used to encode the EBNA 1 protein. Furthermore, DNA encoding the EBNA protein can encode variants of the naturally occurring EBNA 1 amino acid sequence, including those containing, e.g., deletions, additions, insertions, or substitutions, wherein the expressed protein supports replication of EBV oriP-containing episomes in the host cell. This includes, as with other sequences described herein, functionally conservative nucleic acid sequences encoding amino acid sequences conservative variants, sequences having greater than 90%, preferably greater than 95%, identity or homology as determined by BLAST or FASTA algorithms and sequences hybridizing under high stringency hybridization conditions.

Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5X SSC at 65° C.) requires that the sequences exhibit some high degree of complementarily over their entire sequence. Conditions of intermediate stringency (such as, for example, an aqueous solution of 2X SSC at 65° C.) and low stringency (such as, for example, an aqueous solution of 2X SSC at 55° C.), require correspondingly less overall complementarily between the hybridizing sequences. (1X SSC is 0.15 M NaCl, 0.015 M Na citrate.)

Furthermore, degenerate DNA sequences that encode the same EBNA 1 protein can be employed. Degenerate DNA sequences capable of expressing the same amino acid sequence are well known in the art, as are methods of constructing and expressing such DNA sequences.

The gene of interest expressed according to the invention preferably comprises (in a 5'-to-3' direction) (i) a eukaryotic transcriptional promoter operably linked to (ii) a sequence encoding an RNA and/or protein of interest and (iii) a transcriptional termination/polyadenylation sequence. Suitable promoters and transcription termination/polyadenylation sequences include without limitation those described above for kill agonists and antagonists.

Non-limiting examples of genes of interest that can be expressed by employing the invention include genes encoding therapeutic proteins useful in gene therapy, such as cystic fibrosis transmembrane regulator protein, the coding sequence for adenosine deaminase; proteins to be harvested from the transfected cells; and proteins useful in assisting transfected cells in growth, such as insulin and/or transferrin.

In practicing the invention, the episomes may be transfected sequentially, simultaneously, or substantially simultaneously (e.g., prior to clonal selection). It is preferred to transfect two or more episomes at the same time into cells. It is also possible, however, to transfect the episomes sequentially, e.g., one per week. In this embodiment, the episome encoding the kill antagonist is preferably transfected first, followed by the episome encoding the kill agonist. This, however, is not always necessary. For example, the kill agonist can be transfected first where it has been placed under the control of a highly regulatable promoter that can be maintained in a transcriptionally inactive state until the cell has been transfected with both episomes.

The invention also encompasses transfection of an episome encoding a kill antagonist, into a cell having a gene encoding a kill agonist integrated in its chromosomal DNA. In such a system, expression of the kill agonist can be highly regulated by a promoter such that the cell survives in the absence of an appropriate inducer. The episome encoding the kill agonist is transfected into the cell at substantially the same time that the cell is exposed to inducer. Cells that are successfully transfected survive, while cells that are unsuccessfully transfected do not.

"Transfection" as used herein refers to the introduction of DNA into a host cell by any means, and includes without limitation transfection of episomes and other circular DNA forms. This includes methods of gene therapy, such as those described herein. Any appropriate transfection method can be used to practice the invention, including without limitation calcium phosphate co-precipitation, electroporation, gene gun transfection, lipofection or other cationic lipid based transfection. These techniques are well known to those of ordinary skill in the art.

In an embodiment using calcium phosphate precipitation, between about 4 and 20 μg of total DNA are typically used to transfect 0.75–1.5×10$^6$ cells in a T75 flask or 10 cm dish. The can be accomplished for example by diluting 1 μg of episomal mix (e.g., about 0.5 μg of each episome when using two episomes to transfect) with carrier DNA such as sheared salmon sperm, calf thymus, or other inert non-replicating DNA to obtain between 4 and 20 μg of total DNA. Appropriate amounts used in other techniques are known or easily determined by those skilled in this art.

The present invention is useful in both human and veterinary gene therapy applications. The episome or episomes that are to be transfected can be introduced into a treatment subject by methods known in the art, including, for example, liposome formulations introduced parenterally (Zhu et al., *Science* 261:209–211, 1993, or by aerosol (Stribling, *Proc. Natl. Acad. Sci. USA* 89:11277–11281, 1992).

As one example, the present invention can be used for direct gene replacement therapy, as when replacing the function of a non-functional gene (e.g., cystic fibrosis or sickle cell anemia (Hyde et al., *Nature* 362:250–255, 1993). Such direct replacement therapies can be used in veterinary applications as well (Smith, *J. Am. Vet. Med. Assoc.* 204:41–46, 1994; Kay et al., *Proc. Natl. Acad. Sci. USA* 91(6):2353–7, 1994).

In addition the invention can be used to introduce antisense nucleic acids in target cells. Antisense therapy involves the production of nucleic acids that bind to a target nucleic acid, typically an RNA molecule, within cells. In this embodiment, the episomes transfected according to the invention do not necessarily bear a gene of interest, but instead encode RNA that is intended to be therapeutically effective. (Matsukura et al., *Proc. Natl. Acad. Sci. USA* 86:4244–4248, 1989; Agrawal et al., *Proc. Natl. Acad. Sci. USA* 86:7790–7794, 1989; Rittner et al., *Nuc. Acids Res.* 19:1421–1426, 1991;Stein et al, *Science* 261:1004–1012, 1993.)

Sequences that can be targeted for therapeutic applications include: sequences that interact with a regulatory protein (e.g., the interaction of an RNA virus regulatory protein with an RNA genome); and sequences causing inappropriate expression of cellular genes or cell proliferation (e.g., genes associated with cell cycle regulation; genetic disorders; and cancers (protooncogenes)). Potential target sequences include protooncogenes, oncogenes/tumor suppressor genes, transcription factors, and viral genes.

In addition, the invention can be used to deliver DNA sequences encoding catalytic RNA molecules (Castanotto et al., *Critical Reviews in Eukaryotic Gene Expression* 2:331–357, 1992; Lo et al., *Virology* 190:176–183, 1992) into cells. For example, a DNA sequence encoding a ribozyme of interest can be cloned into an episome employed according to the present invention. Such a ribozyme may be a hammerhead ribozyme capable of cleaving a viral substrate, such as the Human Immunodeficiency Virus genome, or an undesirable messenger RNA, such as that of an oncogene.

The present invention encompasses pharmaceutical compositions useful in gene therapy methods. The compositions contain an effective amount of a vector useful to transfect cells according to the invention in combination with a pharmaceutically acceptable carrier.

Vectors administered for gene therapy can be associated with, or contained in lipid/liposome carriers. The use of liposomes to facilitate cellular uptake is described, for example, in U.S. Pat. Nos. 4,897,355 and 4,394,448.

For parenteral administration, sterile liquid pharmaceutical compositions, solutions or suspensions can be employed. Such administration includes, without limitation, intraperitoneal injection, and subcutaneous injection. The compositions can be also be administered intravascularly or via a vascular stent.

In addition, the pharmaceutical compositions employed can be administered by inhalation. A liquid carrier for pressurized compositions can be a halogenated hydrocarbon or another pharmaceutically acceptable propellent. Such pressurized compositions are typically lipid encapsulated or associated for delivery via inhalation. For administration by intranasal or intrabronchial inhalation, the formulation may be an aqueous or partially aqueous solution.

Production of Stably Transformed Cultured Cells

In one series of embodiments, the methods and compositions of the invention are used to achieve stable maintenance of episomes in cells in culture, such as, for example, to effect the stable expression of a protein of interest encoded by a gene present on one of the episomes. In one example of these embodiments, the first plasmid comprises (i) a gene encoding a kill agonist and (ii) a gene encoding a selectable marker for eukaryotic cells, and the second plasmid comprises a gene encoding the cognate kill antagonist. Both plasmids further comprise an EBV oriP sequence, a bacterial origin of replication and a selectable marker for bacteria. Preferably, at least one of the episomes also comprises a gene encoding EBNA1, preferably driven by a strong promoter (e.g. CMV), although it is also possible to transfect the plasmids into cells that endogenously produce EBNA1. The selectable marker for eukaryotic cells insures that cells containing only the second (antagonist-encoding) episome do not survive.

In another embodiment the first plasmid comprises (i) a gene encoding an intracellular, non-secreted, single chain Fv antibody (intrabody) directed against a critical cell component and (ii) a gene encoding a selectable marker for eukaryotic cells, and the second plasmid comprises a gene encoding a variant of the cellular target that is not recognized by the intrabody. Both plasmids preferably further comprise an EBV oriP sequence, a bacterial origin of replication and a selectable marker for bacteria and a gene of interest. At least one of the episomes preferably also comprises a gene encoding an EBNA1 antigen. In this embodiment, as noted above, the intrabody acts as a kill agonist and the gene encoding a variant of the cellular target acts as a kill antagonist.

In yet another embodiment the first plasmid comprises (i) a gene encoding a toxin that targets and inactivates a cellular protein and (ii) a gene encoding a selectable marker for eukaryotic cells, and the second plasmid comprises a gene encoding a version of the cellular target which is resistant to the toxin. Both plasmids preferably further comprise an EBV oriP sequence, a bacterial origin of replication and a selectable marker for bacteria; and at least one of the episomes preferably also comprises a gene encoding an EBNA1 antigen and preferably one episome also comprises a gene of interest. The gene of interest is preferably contained on an episome that does not contain a gene encoding an EBNA1 antigen.

Any eukaryotic cells which support stable replication of the plasmids described above may be used in practicing the invention. Non-limiting examples of host cells for use in the present invention include HEK 293 cells (American Type Culture Collection, Manassas, Va. (ATCC) Deposit Number CRL-1573), CVIEBNA cells (ATCC CRL10478), Hela cells, D98/raji cells, 293EBNA (also referred to herein as "293E cells") available from Invitrogen, Cat. No. R62007, CVI cells (ATCC Cat. No. CCL 70) and 143B cells (ATCC Cat. No. CRL-8303). In addition, primary cultures of eukaryotic cells, such as bone marrow stem cells or liver cells, may be isolated from their tissue of origin and transfected with the episomes according to the invention.

Stable Maintenance of Episomes In Vivo

In another series of embodiments, the methods and compositions of the invention are used to achieve stable maintenance of episomes in cells in vivo, i.e., in an intact organism, such as, e.g., in gene therapy applications. EBV-containing episomes such as those described in U.S. Pat. No. 5,707,830 of Calos can be modified for use in this method. In one example, the first episome comprises a gene encoding a first apoptosis agonist and the second episome comprises a gene encoding the cognate apoptosis antagonist. Additionally, the second episome comprises a gene encoding a second apoptosis agonist, which causes apoptosis by a mechanism distinct from that of the first agonist, and the first episome comprises a gene encoding an apoptosis antagonist that counteracts apoptosis caused by the second agonist. In these embodiments, even in the absence of additional selective pressures, cells containing both episomes survive, while cells transfected with only one episome do not. However, the system advantageously includes selection means for eliminating cells that are transfected with neither episome, e.g., an antibiotic resistance marker encoded by either the first or second episome.

Another embodiment suitable for in vivo maintenance of episomes employs a first episome comprising a gene encoding a toxin that targets and inactivates a cellular protein and the second episome comprising a gene encoding a version of the cellular target which is resistant to the toxin. The second episome also preferably comprises a gene encoding a second toxin that targets and inactivates a different cellular protein than the first toxin, and the first episome comprises a gene encoding a version of the cellular target which is resistant to the second toxin.

Non-Apoptotic Gene Pairs

As noted above, non-apoptotic pairs of proteins can be employed in the invention, such as toxins that act as kill agonists, and resistant versions of the cellular target of the toxin that acts as kill antagonists. An example of such a pair is Diphtheria toxin, or Pseudomonas exotoxin A, and mutant elongation factor 2. Both diphtheria toxin and Pseudomonas exotoxin A inhibit eukaryotic protein synthesis by catalyzing the ADP-ribosylation of elongation factor 2. Diphtheria toxin-resistant versions of the elongation factor 2 gene from Chinese Hamster Ovary (CHO) cells are known. For example, in one such mutated version, the glycine residue at position 717 is mutated to arginine (Kido M, et al. *Cell. Struct. Funct.* 16:447–453, 1991; Omura et al., *Eur. J. Biochem.* 180:1–8, 1989; Kohno et al., J. Biol. Chem. 262: 12298–12305, 1987). In another example, the mutated EF-2 gene contains the following amino acid changes: serine to glycine at position 584, isoleucine to asparagine at position 714, and glycine to aspartic acid at position 719 (Foley et al., *J. Biol. Chem.* 270:23218–23225, 1995). In both of these cases, the amino acid substitutions render the resulting versions of the EF-2 protein highly resistant to the ADP ribosylating effects of diphtheria toxin and Pseudomonas exotoxin A. Homologues of the mutated CHO EF-2 genes described in these references, for example, those derived from other mammalian species, such as human, other primate, or rodent species, can also be employed. Sequences encoding such genes are known. For example, the complete coding sequence for Cricetulus griseus (Chinese hamster) EF-2 is available from GenBank, accession number U17362, locus CGU17362. A complete coding sequence for a suitable diphtheria toxin gene, the Corynebacteriophage beta (*C. diphtheriae*) tox228 gene is available from GenBank, accession number K01723, locus BETDT228, as submitted by Koczorek et al., *Science* 221, 855–858, 1983.

Eukaryotic expression cassettes included in the episomes preferably contain (in a 5'-to-3' direction) a eukaryotic transcriptional promoter operably linked to a protein-coding sequence, splice signals including intervening sequences, and a transcriptional termination/polyadenylation sequence. Promoters suitable for use in EBNA 1-encoding episomes of the invention are those that direct the expression of the DNA encoding the EBNA 1 protein to result in sufficient steady-state levels of EBNA 1 protein to stably maintain EBV oriP-containing episomes.

A "promoter", as that term is used herein, is intended to refer to a sequence that comprises at least a minimal promoter, i.e., any sequence that supports transcription in eukaryotic cells. Non-limiting examples of suitable eukaryotic promoters include early or late viral promoters, such as, for example, SV40 early or late promoters, cytomegalovirus (CMV) immediate early promoters, and Rous Sarcoma Virus (RSV) early promoters; and eukaryotic cell promoters, such as, for example, beta actin promoters (Ng, *Nuc. Acid Res.* 17:601–615, 1989; Quitsche et al., *J. Biol. Chem.* 264:9539–9545, 1989), GADPH promoter (Alexander, M. C. et al., *Proc. Nat. Acad. Sci. USA* 85:5092–5096, 1988, Ercolani, L. et al., *J. Biol. Chem.* 263:15335–15341, 1988), PtK-1 (thymidine kinase) promoter, HSP (heat shock protein) promoters, and any eukaryotic promoter containing a TATA box. Minimal promoter sequences may be derived from these promoters by (i) creating deletion mutants using conventional methods and (ii) testing the ability of the resulting sequences to activate transcription in a cell line. The minimal promoter may be supplemented with additional sequences that enhance transcription and/or confer the ability to specifically regulate transcription by contacting the transformed target cell with exogenous factors. In some cases, inducible promoters require expression of an additional nuclear receptor, which can be encoded by the host cell DNA or by one of the episomes of the present invention. Examples of suitable inducible promoter elements include without limitation: progesterone response element, which is activated by RU486 via the progesterone receptor (Wang et al., *Proc. Natl. Acad. Sci. USA* 91:8180–8184, 1994); metallothionein regulatory elements, which are activated by zinc (Palmiter et al., *Mol. Cell. Biol.* 13:5266–5275, 1993); ecdysone response element, which is activated by ecdysone and ecdysone receptor (commercially available from Invitrogen; see No et al., *Proc. Natl. Acad. Sci. USA* 93:3346–3351, 1993); and tetracycline-responsive promoters (Gossen et al., *Proc. Natl. Acad. Sci. USA* 89;5547–5551, 1992). It will be understood that a particular promoter element may be duplicated and/or present in a different orientation relative to the original promoter from which it was derived. Any promoter that supports an appropriate expression level of kill agonist or antagonist may be used in practicing the invention. Useful transcription termination/polyadenylation sequences include without limitation those derived from the thymidine kinase (tk) gene or SV40-derived sequences, such as found, for example, in the pCEP4 vector (Invitrogen), or human growth hormone (hGH) such as found in vector pcDNA3.1 (Invitrogen).

Strong promoters can be advantageously used to practice of the invention. A "strong promoter" is one which results in a net steady-state concentration of RNA approximately 0.25 times the steady-state level of GAPDH or greater. The following formula can be used to determine promoter activity in most cell types: promoter activity is acceptable if (RNA concentration of episomally derived gene)/(GADPH steady state RNA)$\geq 0.25$. Alternatively, if GAPDH is present in exceptionally low quantities in a given cell type, the steady-state concentration of beta actin can be substituted instead. This formula takes into account the number of episomes that may be present within the cell, which normally varies between about 1 and 60 copies, and normally averages about 10 copies (Margolskee et al., *Curr. Topics in Microb. and Immunol* 158, 67–95, 1992.;Yates et al., *Nature*. 313:812–815, 1985).

Non-limiting examples of such "strong promoters" include early or late viral promoters, such as, e.g, SV40 early or late promoters, cytomegalovirus (CMV) immediate early promoters, Rous Sarcoma Virus (RSV) early promoters; eukaryotic cell promoters, such as, e.g., beta actin promoter, GADPH promoter, metallothionein promoter (Karin et al. *Cell* 36: 371–379, 1989; Richards et al., *Cell* 37: 263–272, 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at GenBank, accession no. XO5244, nucleotide 283–341) or a mouse mammary tumor promoter (available from the ATCC, Cat. No. ATCC 45007).

Selectable marker genes for use in the episomes employed in the invention include those that encode proteins conferring resistance to specific antibiotics and/or factors that allow cells harboring these genes to grow in the presence of the cognate antibiotics or factors. Suitable eukaryotic selectable markers also include essential amino acid-synthesizing enzymes, e.g., glutamine synthase.

A selectable marker for eukaryotic cells is preferably included on at least one of the episomes employed in the present invention. This marker is advantageously used when the episome is first inserted into the cell to select for cells that have been successfully transfected. The marker is also advantageously used to kill parental (non-transfected) cells. Non-limiting examples of suitable eukaryotic selectable markers include antibiotic resistance genes conferring resistance to hygromycin (hyg or hph, commercially available from Life Technologies, Inc.); neomycin (neo, commercially available from Life Technologies, Inc.); zeocin (Sh Ble, commercially available from Pharmingen, San Diego Calif.); puromycin (pac, puromycin-N-acetyl-transferase, available from Clontech, Palo Alto Calif.), ouabain (oua, available from Pharmingen) and blasticidin (available from Invitrogen). A marker that allows cell sorting, such as cell sorting based on magnetic means, can also be employed.

Non-limiting examples of selectable marker genes for use in bacteria include antibiotic resistance genes conferring resistance to ampicillin, tetracycline and kanamycin. The tetracycline (tet) and ampicillin (amp) resistance marker genes can be obtained from any of a number of commercially available vectors including pBR322 (available from New England BioLabs, Beverly, Mass., cat. no. 303-3s). The tet coding sequence is contained within nucleotides 86–476; the amp gene is contained within nucleotides 3295–4155.

The nucleotide sequence of the kanamycin (kan) gene is available from vector pACYC 177, from New England BioLabs, Cat no. 401-L, GenBank accession No. X06402.

The episomes can encode a reporter gene, such as a luciferase gene. Examples of DNA sequences encoding luciferase genes are described by Wood et al., *Science* 244:700–702, 1989; Zenno et al.,U.S. Pat. No. 5,618,772; and *Proc. Natl. Acad. Sci. USA*, 82:7870–7873, 1985. Reporter genes that can also be used include green fluorescent protein (GFP, Clontech, Cat. No. 60771), secreted alkaline phosphatase (SEAP, pSEAP2-Basic, Clontech, Cat. No. 6049-1), growth hormone (which can be measured by ELISA), chloramphenicol acetyl transferase (CAT, available from Promega, Madison, Wis., pCAT(Tm)-3-Basic Vector Cat. No. E1041), beta-lactamase, and beta-galactosidase.

Elements can be coded for in an episome that respond to transduction signals. Cre elements (a 6-fold repeat of cyclic AMP response elements available from Stratagene in phagemid vector pCRE-Luc, Cat. No. 219076) can be used to respond to changes in intracellular cAMP concentrations. Alternately, serum response elements (SRE, Stratagene phagemid vector pSRE-Luc. Cat. No. 219080), nuclear factor kB (NF-kB, Stratagene phagemid vector pNFKB-Luc Cat. No. 219078), activator protein 1 (AP-1, Stratagene phagemid vector pAP-1-Luc, Cat. No. 219074) and serum response factor elements (Stratagene phagemid vector pSRF-Luc, Cat. No. 219082), can be encoded.

Episomes can be employed in the invention to transfect any suitable cells, including primate, canine, porcine, and other permissive cell types. EBNA 1 can be stably transfected into any primate or canine cell using well known techniques, and the resulting cell line that expresses EBNA 1 from an integrated gene copy can be used to support replication of multiple episomes. Alternately, a cell line that already harbors infectious or defective EBV can be used, as long as EBNA 1 is expressed. This includes many EBV transformed lymphoblasts available from the ATCC. As discussed above, it is also possible to express EBNA 1 from a stably transfected episome.

Recombinant cell lines of the invention containing multiple episomes are advantageously used in assays to identify drug candidates. Compounds assayed can be derived from combinatorial libraries on polymer beads. For example, library compounds can be eluted from the beads and evaporated to dryness in microliter plates in preparation for an assay using the cells. Compounds on beads can be released by photocleavage, or another type of cleavage. Cleavage of photocleavable linkers is preferred. Such linkers, and methods for their cleavage, are described in Barany et al. (1985) *J. Am. Chem. Soc.* 107:4936. Examples of other linkers and the relevant cleavage reagents are described in WO 94/08051.

Using combinatorial libraries prepared on beads, the identity of active compounds is preferably determined using the encoding system described in U.S. Pat. Nos. 5,721,099 and 5,565,324. In this system, chemical tags encoding the identities of the compounds are applied to the solid supports. The identity of the compound on a given support can be determined by detaching the chemical tags from the support, identifying the tags by, e.g., gas chromatography, and correlating the identities of tags with the identity of the compound. Once an active compound is identified, the corresponding bead (which had contained the compound) can be examined, and the identity of the compound determined by releasing the tags and decoding by this method.

The present invention is described below in specific examples which are intended to further describe the invention without limiting the scope thereof.

EXAMPLE 1

Construction of Expression Vectors

In this experiment, bcl2 and bad; and dff45 and cide-a are employed as kill antagonist and kill agonist pairs in episomes used to transfect eukaryotic cells. The steps described below, and schematically depicted in FIGS. 3A, 3B, 3C, and 3D, are employed in order to construct the episomes.

1. The SV40 promoter (pSV) is PCR amplified with Clal-NheI and AgeI ends. The promoter is amplified with oligos
ggccatcgatgctagccagctgtggaatgtgtgtcag (SEQ ID NO. 5) and ccggaccggtaagcttttgcaaaagcctaggc (SEQ ID NO. 6). The PCR amplified SV40 promoter (pSV) fragment is digested with ClaI and AgeI and the CMV promoter in vector pE3dhyg (1) is replaced, by digesting with ClaI and AgeI, to make construct pESVdhyg (2).

2. A new multicloning site 2 (mcs2) (NheI-SwaI-XhoI with BspLU11I overhangs) is added to a fresh aliquot of BspLU11I cut pE3dhyg (1) vector to make pE6nlΔ (4) and to pE3hyg (3) to make pE6nl (5). This is accomplished using the oligonucleotides shown below, i.e., the oligonucleotides are annealed and ligated into BspLu11I-cut pE3hyg to create strands that are compatible with the added genes: catgttggctagccattaaatcctcgagga (SEQ ID NO. 7) and catgtcctcgaggatttaaatggctagccaa (SEQ ID NO. 8).

3. mcs3 in pESVdhyg (2) is replaced with mcs7 (which contains [AgeI overhang]-BsiWI-NheI-Sse83871-BspEI-AflII-XmaIII-[Xba overhang] to make pE7SV (6). This is accomplished by digesting vector pESVdhyg (2) with the unique restriction sites AgeI and XbaI and reconstituting the new mcs7 using oligos
ccggtcgtacggctagccctgcaggtccggacttaagcggccgt (SEQ ID NO. 9) and
ctagacggccgcttaagtccggacctgcagggctagccgtacga (SEQ ID NO 10).

The NsiI-XmaI IRES fragment from pIRES-eyfp (Clontech, Palo Alto, Calif.) is cloned into the compatible Sse83871 and BspEI cut pE7SV (6) mcs sites, respectively, to make pE7SVIRES (7). All four of the restriction sites used in this step are destroyed.

4. The cDNAs encoding the apoptotic proteins used in this experiment, bcl2, dff45, bad, and cide-a are RT-PCR amplified from appropriate tissue sources. Such sources are determined, e.g., by searching the Genbank database for the relevant information. For example, cide-a is RT-PCR amplified from human heart cDNA, bad from testis, breast, colon, or spleen cDNA, and dff45 from Jurkat T-cell leukemia, HeLa carcinoma, SK-N-MC neuroblastoma, or WI-38 embryonic lung fibroblast cDNA. bcl2 and dff45 cDNAs have BsiWI and NheI restriction sites incorporated at the 5' and 3' ends, respectively, and bad, and cide-a have AflII and XmaIII sites added to the 5' and 3' ends, respectively. The oligos shown below are used for the PCR step; start and stop codons are shown in upper case.

Bcl2 5' oligo: aattcgtacgaccATGgcgcacgctgggagaac (SEQ ID NO. 11)
Bcl2 3' oligo: aattgctagcctTCActtgtggctcagatagg (SEQ ID NO. 12)
Dff45 5' oligo: aattcgtacgaccATGgaggtgaccggggacg (SEQ ID NO. 13)
Dff45 3' oligo: aattgctagcCTAtgtgggatcctgtctggc (SEQ ID NO. 14)
Bad 5' oligo: aattcttaagaccATCttccagatcccagagttg (SEQ ID NO. 15)
Bad 3' oligo: aattcggccgTCActgggaggggggcggag (SEQ ID NO. 16)
cide-a 5' oligo: aattcttaagaccATGgaggccgcccgggact (SEQ ID NO. 17)
cide-a 3' oligo: aattcggccgCTAtccacacgtgaacctgc (SEQ ID NO. 18)

5. bcl2 and dff45 are cloned into separate pE7SVIRES (7) vectors to generate pdffIRES (8) and pbclIRES (9). This is accomplished by digesting the bcl2 and dff45 RT-PCR fragments and vector pE7SVIRES (7) with BsiWI and NheI and cloning the former into the latter. In addition, the BsiWI and NheI cut bcl2 and dff45 fragments are cloned into separate Acc65I and XbaI pcDNA3.1zeo vectors (Invitrogen) to generate helper vectors pcDNAzbcl (11) and pcDNAzdff (10). (BsiWI and Acc65I have compatible overhangs that ligate together without recreating either of the restriction sites. The same is true for NheI and XbaI.)

6. The RT-PCR generated bad fragments are cloned into pdffIRES (8) to generate pdffIRESbad (12). This is accomplished by digesting bad and pdffIRES (8) with AflII and XmaIII and cloning the former into the latter.

7. The RT-PCR generated cide-a is cloned into pbcl IRES (9) to generate pbciIREScide (13). This is accomplished by digesting cide-a and pbc1IRES (9) and AflII and XmaIII and cloning the former into the latter.

8. LacZ is cloned into vector pE6nlΔ (4). This is accomplished by reclaiming the LacZ fragment from vector p324 (Colberg-Poley et al. *J. Virol.* 66: 95–105, 1992) with PstI and XbaI and subcloning this piece into Sse83871+XbaI cut pE6nlΔ (4) to generate vector pE6nlac (14) (Sse83871 and PstI are compatible sites).

9. The fragment encoding pSV-dff-IRES-bad-IVS-p(A) (12) is excised from vector pdffIRESbad (12) with NheI and SalI, cloned into the compatible NheI and XhoI sites of pE6nlac (14) to generate pE6dffbadlac (15). This is one of the two final constructs.

10. EBNA1 is cloned into vector pE6nl (5) to generate vector pE6EBNA (16). This is accomplished by reclaiming the EBNAI fragment from vector pCMVEBNA (from Invitrogen, cat. no. V200-10) with KpnI and Sse83871 and subcloning this piece into KpnI+Sse83871 cut pE6nl (5).

11. The fragment pSV-bcl-IRES-cide-IVS-p(A) with NheI and SalI is excised, cloned into the compatible NheI and XhoI site of pE6EBNA (16) to generate pE6bclcideEBNA (17).

This is the second of two final constructs.

Experimental Procedures

Constructs pE6bclcideEBNA and pE6dffbadlac are transfected simultaneously, and stoichiometrically, into 293E cells (293EBNA cell line, cat. no. R620-07, Invitrogen). Selection with the antibiotic hygromycin at 250 ug/ml commences at 48 hours after transfection.

To ensure that the transfected cells live long enough to be able to stably harbor the two mutually selecting episomes, an additional precaution can be taken: a second transfection is performed on a different aliquot of 293E cells. This transfection includes constructs pE6bclcideEBNA and pE6dffbadlac, and the helper constructs pcDNAzbcl, and pcDNAzdff. The stoichiometry is 1:1:10:10. The helper constructs employed are non-replicating (they contain no oriP encoding sequence) and are not selected as zeocin is not included in the media. By including a 10-fold molar excess of helper constructs, the transfected cells transiently produce an excess of apoptotic antagonist proteins bcl2 and dff45. By the time these constructs are lost from the cell population (normally within a week or two), the episomal constructs are stably established in the surviving cell population.

Results

Selection with hygromycin substantially eliminates cells that have not incorporated the vector pE5bclcideEBNA. Likewise, any cell that does not harbor vector pE6dffbadlac is substantially eliminated due to the expression of cide from pE6bclcideEBNA. The presence of dff from pE6dffbadlac protects the cell from apoptosis. After the episomes stably reside in the cell for ~2 weeks in hygromycin selection, the exposure to antibiotics is discontinued.

The presence of both episomes is required for cell survival. The first, pE6bclcideEBNA, provides three gene products: EBNA1, required for the maintenance of both episomes; bcl2 which protects the cell from bad; and cide-a which causes the cell to undergo apoptosis in the absence of dff45. The second vector, pE6dffbadlac, also provides three gene products: lacz, which provides a convenient means for monitoring the cells and would normally be substituted for by another gene, the expression of which is desired; dff45 which protects the cell from the apoptotic action of cide-a; and bad, the presence of which induces apoptosis in the absence of bcl2 (provided by the first episome, pE6bclcideEBNA).

In both cases described above, the partner providing the antagonist of apoptosis function is positioned 5' to the internal ribosome entry site (IRES) sequence while the gene providing the apoptotic function is situated 3' to the IRES sequence. This helps to ensure that there will be more, stoichiometrically, of the protecting function of the antagonist protein than of the killing function of the agonist protein.

An IRES sequence can also be advantageously positioned between two components of a gene of interest, e.g., components expressing receptor subunits. It is also possible to position two strong back to back promoters between the two components of the gene to ensure that both are adequately expressed.

Other aspects of the present invention will be apparent to those skilled in this art.

SEQUENCE LISTING

<160> NUMBER OF SEQ ID NOS: 18

<210> SEQ ID NO 1
<211> LENGTH: 1936
<212> TYPE: DNA
<213> ORGANISM: Epstein Barr Virus
<220> FEATURE:
<221> NAME/KEY: rep_origin
<222> LOCATION: (1)..(1936)
<223> OTHER INFORMATION: EBV origin of replication

<400> SEQUENCE: 1

```
gcatgcagga aaaggacaag cagcgaaaat tcacgccccc ttgggaggtg gcggcatatg      60
caaaggatag cactcccact ctactactgg gtatcatatg ctgactgtat atgcatgagg     120
atagcatatg ctacccggat acagattagg atagcatata ctacccagat atagattagg     180
atagcatatg ctacccagat atagattagg atagcctatg ctacccagat ataaattagg     240
atagcatata ctacccagat atagattagg atagcatatg ctacccagat atagattagg     300
atagcctatg ctacccagat atagattagg atagcatatg ctacccagat atagattagg     360
atagcatatg ctatccagat atttgggtag tatatgctac ccagatataa attaggatag     420
catatactac cctaatctct attaggatag catatgctac ccggatacag attaggatag     480
catatactac ccagatatag attaggatag catatgctac ccagatatag attaggatag     540
cctatgctac ccagatataa attaggatag catatactac ccagatatag attaggatag     600
catatgctac ccagatatag attaggatag cctatgctac ccagatatag attaggatag     660
catatgctat ccagatattt gggtagtata tgctacccat ggcaacatta gcccaccgtg     720
ctctcagcga cctcgtgaat atgaggacca acaaccctgt gcttggcgct caggcgcaag     780
tgtgtgtaat ttgtcctcca gatcgcagca atcgcgcccc tatcttggcc cgcccaccta     840
cttatgcagg tattccccgg ggtgccatta gtggttttgt gggcaagtgg tttgaccgca     900
gtggttagcg gggttacaat cagccaagtt attacaccct tattttacag tccaaaaccg     960
cagggcggcg tgtgggggct gacgcgtgcc cccactccac aatttcaaaa aaaagagtgg    1020
ccacttgtct ttgtttatgg gccccattgg cgtggagccc cgtttaattt tcgggggtgt    1080
tagagacaac cagtggagtc cgctgctgtc ggcgtccact ctctttcccc ttgttacaaa    1140
tagagtgtaa caacatggtt cacctgtctt ggtccctgcc tgggacacat cttaataacc    1200
ccagtatcat attgcactag gattatgtgt tgcccatagc cataaattcg tgtgagatgg    1260
acatccagtc tttacggctt gtccccaccc catggatttc tattgttaaa gatattcaga    1320
atgtttcatt cctacactag tatttattgc ccaagggggtt tgtgagggtt atattggtgt    1380
catagcacaa tgccaccact gaaccccccg tccaaatttt attctggggg cgtcacctga    1440
```

-continued

```
aaccttgttt tcgagcacct cacatacacc ttactgttca caactcagca gttattctat    1500
tagctaaacg aaggagaatg aagaagcagg cgaagattca ggagagttca ctgcccgctc    1560
cttgatcttc agccactgcc cttgtgacta aaatggttca ctaccctcgt ggaatcctga    1620
ccccatgtaa ataaaaccgt gacagctcat ggggtgggag atatcgctgt tccttaggac    1680
ccttttacta accctaattc gatagcatat gcttcccgtt gggtaacata tgctattgaa    1740
ttagggttag tctggatagt atatactact acccgggaag catatgctac ccgtttaggg    1800
ttaacaaggg ggccttataa acactattgc taatgccctc ttgagggtcc gcttatcggt    1860
agctacacag gcccctctga ttgacgttgg tgtagcctcc cgtagtcttc ctgggcccct    1920
gggaggtaca tgtccc                                                    1936

<210> SEQ ID NO 2
<211> LENGTH: 1926
<212> TYPE: DNA
<213> ORGANISM: Epstein Barr Virus
<220> FEATURE:
<221> NAME/KEY: CDS
<222> LOCATION: (1)..(1926)
<223> OTHER INFORMATION: coding strand of EBNA-1 DNA

<400> SEQUENCE: 2 atg tct gac gag ggg cca ggt aca gga cct gga aat ggc cta gga gag     48
Met Ser Asp Glu Gly Pro Gly Thr Gly Pro Gly Asn Gly Leu Gly Glu
1               5                   10                  15 aag gga gac aca tct gga cca gaa ggc tcc ggc ggc agt gga cct caa     96
Lys Gly Asp Thr Ser Gly Pro Glu Gly Ser Gly Gly Ser Gly Pro Gln
                20                  25                  30 aga aga ggg ggt gat aac cat gga cga gga cgg gga aga gga cga gga    144
Arg Arg Gly Gly Asp Asn His Gly Arg Gly Arg Gly Arg Gly Arg Gly
            35                  40                  45 cga gga ggc gga aga cca gga gcc ccg ggc ggc tca gga tca ggg cca    192
Arg Gly Gly Gly Arg Pro Gly Ala Pro Gly Gly Ser Gly Ser Gly Pro
        50                  55                  60 aga cat aga gat ggt gtc cgg aga ccc caa aaa cgt cca agt tgc att    240
Arg His Arg Asp Gly Val Arg Arg Pro Gln Lys Arg Pro Ser Cys Ile
65                  70                  75                  80 ggc tgc aaa ggg acc cac ggt gga aca gga gca gga gca gga gcg gga    288
Gly Cys Lys Gly Thr His Gly Gly Thr Gly Ala Gly Ala Gly Ala Gly
                85                  90                  95 ggg gca gga gca gga ggg gca gga gca gga gga ggg gca gga gca gga    336
Gly Ala Gly Ala Gly Gly Ala Gly Ala Gly Gly Gly Ala Gly Ala Gly
                100                 105                 110 gga ggg gca gga ggg gca gga ggg gca gga ggg gca gga gca gga gga    384
Gly Gly Ala Gly Gly Ala Gly Gly Ala Gly Gly Ala Gly Ala Gly Gly
            115                 120                 125 ggg gca gga gca gga gga ggg gca gga ggg gca gga ggg gca gga gca    432
Gly Ala Gly Ala Gly Gly Gly Ala Gly Gly Ala Gly Gly Ala Gly Ala
        130                 135                 140 gga gga ggg gca gga gca gga ggg gca gga ggg gca gga gca gga ggg    480
Gly Gly Gly Ala Gly Ala Gly Gly Ala Gly Gly Ala Gly Ala Gly Gly
145                 150                 155                 160 gga ggg gca gga ggg gca gga ggg gca gga gca gga ggg gca gga       528
Gly Gly Ala Gly Gly Ala Gly Gly Ala Gly Ala Gly Gly Ala Gly
                165                 170                 175 gca gga gga ggg gca gga ggg gca gga gca gga gga ggg gca gga ggg    576
Ala Gly Gly Gly Ala Gly Gly Ala Gly Ala Gly Gly Gly Ala Gly Gly
            180                 185                 190 gca gga ggg gca gga gca gga gga ggg gca gga gca gga ggg gca gga    624
```

-continued

```
Ala Gly Gly Ala Gly Ala Gly Gly Ala Gly Ala Gly Gly Ala Gly
            195                 200                 205 ggg gca gga ggg gca gga gca gga ggg gca gga gca gga ggg gca        672
Gly Ala Gly Gly Ala Gly Ala Gly Gly Ala Gly Ala Gly Gly Ala
210                 215                 220 gga ggg gca gga ggg gca gga gca gga ggg gca gga gca gga ggg gca    720
Gly Gly Ala Gly Gly Ala Gly Ala Gly Gly Ala Gly Ala Gly Gly Ala
225                 230                 235                 240 gga gca gga ggg gca gga gca gga ggg gca gga ggg gca gga gca gga    768
Gly Ala Gly Gly Ala Gly Ala Gly Gly Ala Gly Gly Ala Gly Ala Gly
                245                 250                 255 ggg gca gga ggg gca gga gca gga ggg gca gga ggg gca gga gca gga    816
Gly Ala Gly Gly Ala Gly Ala Gly Gly Ala Gly Gly Ala Gly Ala Gly
            260                 265                 270 gga ggg gca gga ggg gca gga gca gga gga ggg gca gga ggg gca gga    864
Gly Gly Ala Gly Gly Ala Gly Ala Gly Gly Gly Ala Gly Gly Ala Gly
        275                 280                 285 gca gga ggg gca gga ggg gca gga gca gga ggg gca gga ggg gca gga    912
Ala Gly Gly Ala Gly Gly Ala Gly Ala Gly Gly Ala Gly Gly Ala Gly
290                 295                 300 gca gga ggg gca gga ggg gca gga gca gga gga ggg gca gga gca gga    960
Ala Gly Gly Ala Gly Gly Ala Gly Ala Gly Gly Gly Ala Gly Ala Gly
305                 310                 315                 320 ggg gca gga gca gga ggt gga ggc cgg ggt cga gga ggc agt gga ggc    1008
Gly Ala Gly Ala Gly Gly Gly Gly Arg Gly Arg Gly Gly Ser Gly Gly
                325                 330                 335 cgg ggt cga gga ggt agt gga ggc cgg ggt cga gga ggt agt gga ggc    1056
Arg Gly Arg Gly Gly Ser Gly Gly Arg Gly Arg Gly Gly Ser Gly Gly
            340                 345                 350 cgc cgg ggt aga gga cgt gaa aga gcc agg ggg gga agt cgt gaa aga    1104
Arg Arg Gly Arg Gly Arg Glu Arg Ala Arg Gly Gly Ser Arg Glu Arg
        355                 360                 365 gcc agg ggg aga ggt cgt gga cgt gga gaa aag agg ccc agg agt ccc    1152
Ala Arg Gly Arg Gly Arg Gly Arg Gly Glu Lys Arg Pro Arg Ser Pro
370                 375                 380 agt agt cag tca tca tca tcc ggg tct cca ccg cgc agg ccc cct cca    1200
Ser Ser Gln Ser Ser Ser Ser Gly Ser Pro Pro Arg Arg Pro Pro Pro
385                 390                 395                 400 ggt aga agg cca ttt ttc cac cct gta ggg gaa gcc gat tat ttt gaa    1248
Gly Arg Arg Pro Phe Phe His Pro Val Gly Glu Ala Asp Tyr Phe Glu
                405                 410                 415 tac cac caa gaa ggt ggc cca gat ggt gag cct gac gtg ccc ccg gga    1296
Tyr His Gln Glu Gly Gly Pro Asp Gly Glu Pro Asp Val Pro Pro Gly
            420                 425                 430 gcg ata gag cag ggc ccc gca gat gac cca gga gaa ggc cca agc act    1344
Ala Ile Glu Gln Gly Pro Ala Asp Asp Pro Gly Glu Gly Pro Ser Thr
        435                 440                 445 gga ccc cgg ggt cag ggt gat gga ggc agg cgc aaa aaa gga ggg tgg    1392
Gly Pro Arg Gly Gln Gly Asp Gly Gly Arg Arg Lys Lys Gly Gly Trp
450                 455                 460 ttt gga aag cat cgt ggt caa gga ggt tcc aac ccg aaa ttt gag aac    1440
Phe Gly Lys His Arg Gly Gln Gly Gly Ser Asn Pro Lys Phe Glu Asn
465                 470                 475                 480 att gca gaa ggt tta aga gct ctc ctg gct agg agt cac gta gaa agg    1488
Ile Ala Glu Gly Leu Arg Ala Leu Leu Ala Arg Ser His Val Glu Arg
                485                 490                 495 act acc gac gaa gga act tgg gtc gcc ggt gtg ttc gta tat gga ggt    1536
Thr Thr Asp Glu Gly Thr Trp Val Ala Gly Val Phe Val Tyr Gly Gly
            500                 505                 510
```

-continued

```
agt aag acc tcc ctt tac aac cta agg cga gga act gcc ctt gct att      1584
Ser Lys Thr Ser Leu Tyr Asn Leu Arg Arg Gly Thr Ala Leu Ala Ile
    515                 520                 525 cca caa tgt cgt ctt aca cca ttg agt cgt ctc ccc ttt gga atg gcc      1632
Pro Gln Cys Arg Leu Thr Pro Leu Ser Arg Leu Pro Phe Gly Met Ala
530                 535                 540 cct gga ccc ggc cca caa cct ggc ccg cta agg gag tcc att gtc tgt      1680
Pro Gly Pro Gly Pro Gln Pro Gly Pro Leu Arg Glu Ser Ile Val Cys
545                 550                 555                 560 tat ttc atg gtc ttt tta caa act cat ata ttt gct gag gtt ttg aag      1728
Tyr Phe Met Val Phe Leu Gln Thr His Ile Phe Ala Glu Val Leu Lys
                565                 570                 575 gat gcg att aag gac ctt gtt atg aca aag ccc gct cct acc tgc aat      1776
Asp Ala Ile Lys Asp Leu Val Met Thr Lys Pro Ala Pro Thr Cys Asn
            580                 585                 590 atc agg gtg act gtg tgc agc ttt gac gat gga gta gat ttg cct ccc      1824
Ile Arg Val Thr Val Cys Ser Phe Asp Asp Gly Val Asp Leu Pro Pro
        595                 600                 605 tgg ttt cca cct atg gtg gaa ggg gct gcc gcg gag ggt gat gac gga      1872
Trp Phe Pro Pro Met Val Glu Gly Ala Ala Ala Glu Gly Asp Asp Gly
610                 615                 620 gat gac gga gat gaa gga ggt gat gga gat gag ggt gag gaa ggg cag      1920
Asp Asp Gly Asp Glu Gly Gly Asp Gly Asp Glu Gly Glu Glu Gly Gln
625                 630                 635                 640 gag tga                                                              1926
Glu
```

<210> SEQ ID NO 3
<211> LENGTH: 641
<212> TYPE: PRT
<213> ORGANISM: Epstein Barr Virus

<400> SEQUENCE: 3

```
Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly Gly
            100                 105                 110

Gly Ala Gly Gly Ala Gly Gly Ala Gly Gly Ala Gly Ala Gly Gly
        115                 120                 125

Gly Ala Gly Ala Gly Gly Ala Gly Gly Ala Gly Gly Ala Gly Ala
    130                 135                 140

Gly Gly Gly Ala Gly Ala Gly Gly Ala Gly Gly Ala Gly Ala Gly
145                 150                 155                 160

Gly Gly Ala Gly Gly Ala Gly Gly Ala Gly Ala Gly Gly Ala Gly
                165                 170                 175

Ala Gly Gly Gly Ala Gly Gly Ala Gly Ala Gly Gly Gly Ala Gly Gly
            180                 185                 190
```

-continued

```
Ala Gly Gly Ala Gly Ala Gly Gly Ala Gly Ala Gly Gly Ala Gly
        195                 200                 205
Gly Ala Gly Gly Ala Gly Ala Gly Gly Ala Gly Ala Gly Gly Ala
        210                 215                 220
Gly Gly Ala Gly Gly Ala Gly Ala Gly Gly Ala Gly Ala Gly Gly Ala
225                 230                 235                 240
Gly Ala Gly Gly Ala Gly Ala Gly Gly Ala Gly Ala Gly Gly Ala Gly
                245                 250                 255
Gly Ala Gly Gly Ala Gly Ala Gly Gly Ala Gly Ala Gly Gly Ala Gly
                260                 265                 270
Gly Gly Ala Gly Gly Ala Gly Ala Gly Gly Ala Gly Gly Ala Gly
        275                 280                 285
Ala Gly Gly Ala Gly Ala Gly Gly Ala Gly Gly Ala Gly Gly Ala Gly
        290                 295                 300
Ala Gly Gly Ala Gly Ala Gly Ala Gly Gly Ala Gly Ala Gly
305                 310                 315                 320
Gly Ala Gly Ala Gly Gly Gly Arg Gly Arg Gly Gly Ser Gly Gly
                325                 330                 335
Arg Gly Arg Gly Gly Ser Gly Gly Arg Gly Arg Gly Gly Ser Gly Gly
                340                 345                 350
Arg Arg Gly Arg Gly Arg Glu Arg Ala Arg Gly Gly Ser Arg Glu Arg
                355                 360                 365
Ala Arg Gly Arg Gly Arg Gly Arg Gly Glu Lys Arg Pro Arg Ser Pro
370                 375                 380
Ser Ser Gln Ser Ser Ser Ser Gly Ser Pro Arg Arg Pro Pro Pro
385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
                420                 425                 430
Ala Ile Glu Gln Gly Pro Ala Asp Asp Pro Gly Glu Gly Pro Ser Thr
                435                 440                 445
Gly Pro Arg Gly Gln Gly Asp Gly Gly Arg Arg Lys Lys Gly Gly Trp
        450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
                500                 505                 510
Ser Lys Thr Ser Leu Tyr Asn Leu Arg Arg Gly Thr Ala Leu Ala Ile
        515                 520                 525
Pro Gln Cys Arg Leu Thr Pro Leu Ser Arg Leu Pro Phe Gly Met Ala
        530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
                580                 585                 590
Ile Arg Val Thr Val Cys Ser Phe Asp Asp Gly Val Asp Leu Pro Pro
                595                 600                 605
Trp Phe Pro Pro Met Val Glu Gly Ala Ala Ala Glu Gly Asp Asp Gly
```

| | | | |
|---|---|---|---|
| | 610 | 615 | 620 |

Asp Asp Gly Asp Glu Gly Gly Asp Gly Asp Glu Gly Glu Glu Gly Gln
625              630              635              640

Glu

<210> SEQ ID NO 4
<211> LENGTH: 1926
<212> TYPE: DNA
<213> ORGANISM: Epstein Barr Virus
<220> FEATURE:
<221> NAME/KEY: misc_feature
<222> LOCATION: (1)..(1926)
<223> OTHER INFORMATION: template strand of EBNA-1 DNA

<400> SEQUENCE: 4

| | |
|---|---|
| tacagactgc tccccggtcc atgtcctgga cctttaccgg atcctctctt ccctctgtgt | 60 |
| agacctggtc ttccgaggcc gccgtcacct ggagtttctt ctcccccact attggtacct | 120 |
| gctcctgccc cttctcctgc tcctgctcct ccgccttctg gtcctcgggg cccgccgagt | 180 |
| cctagtcccg gttctgtatc tctaccacag gcctctgggg tttttgcagg ttcaacgtaa | 240 |
| ccgacgtttc cctgggtgcc accttgtcct cgtcctcgtc ctcgccctcc ccgtcctcgt | 300 |
| cctccccgtc ctcgtcctcc tcccgtcct gtcctcctc ccgtcctcc ccgtcctccc | 360 |
| cgtcctcccc gtcctcgtcc tcctcccgt ctcgtcctc ctcccgtcc tccccgtcct | 420 |
| ccccgtcctc gtcctcctcc ccgtcctcgt ctcctcccc gtcctcccg tcctcgtcct | 480 |
| cctcccgtc ctccccgtcc tccccgtcct cgtcctcctc ccgtcctcg tcctcctccc | 540 |
| cgtcctcccc gtcctcgtcc tcctcccgt ctccccgtc ctccccgtcc tgtcctcct | 600 |
| cccgtcctc gtcctccccg tcctccccgt cctccccgtc ctcgtcctcc ccgtcctcgt | 660 |
| cctcctcccc gtcctccccg tcctccccgt cctcgtcctc ccgtcctcg tcctccccgt | 720 |
| cctcgtcctc ccgtcctcg tcctccccgt cctccccgtc ctcgtcctcc ccgtcctccc | 780 |
| cgtcctcgtc ctccccgtcc tccccgtcct cgtcctcctc ccgtcctcc ccgtcctcgt | 840 |
| cctcctcccc gtcctccccg tcctcgtcct ccccgtcctc ccgtcctcg tcctccccgt | 900 |
| cctcccccgtc ctcgtcctcc ccgtcctccc gtcctcgtc ctcctcccg tcctcgtcct | 960 |
| ccccgtcctc gtcctccacc tccggcccca gctcctccgt cacctccggc ccagctcct | 1020 |
| ccatcacctc cggccccagc tcctccatca cctccggcgg ccccatctcc tgcactttct | 1080 |
| cggtcccccc cttcagcact ttctcggtcc ccctctccag cacctgcacc tcttttctcc | 1140 |
| gggtcctcag ggtcatcagt cagtagtagt aggcccagag gtggcgcgtc cggggaggt | 1200 |
| ccatcttccg gtaaaaaggt gggacatccc cttcggctaa taaaacttat ggtggttctt | 1260 |
| ccaccgggtc taccactcgg actgcacggg ggccctcgct atctcgtccc ggggcgtcta | 1320 |
| ctgggtcctc ttccggggttc gtgacctggg gccccagtcc cactacctcc gtccgcgttt | 1380 |
| tttcctccca ccaaaccttt cgtagcacca gttcctccaa ggttgggctt taaactcttg | 1440 |
| taacgtcttc caaattctcg agaggaccga tcctcagtgc atctttcctg atggctgctt | 1500 |
| ccttgaaccc agcggccaca caagcatata cctccatcat tctggaggga aatgttggat | 1560 |
| tccgctcctt gacgggaacg ataaggtgtt acagcagaat gtggtaactc agcagagggg | 1620 |
| aaaccttacc ggggacctgg gccgggtgtt ggaccgggcg attccctcag gtaacagaca | 1680 |
| ataaagtacc agaaaaatgt ttgagtatat aaacgactcc aaaacttcct acgctaattc | 1740 |
| ctggaacaat actgtttcgg gcgaggatgg acgttatagt cccactgaca cacgtcgaaa | 1800 |

```
ctgctacctc atctaaacgg agggaccaaa ggtggatacc accttccccg acggcgcctc    1860
ccactactgc ctctactgcc tctacttcct ccactacctc tactcccact ccttcccgtc    1920
ctcact                                                                1926

<210> SEQ ID NO 5
<211> LENGTH: 37
<212> TYPE: DNA
<213> ORGANISM: artificial sequence
<220> FEATURE:
<221> NAME/KEY: misc_feature
<222> LOCATION: (1)..(37)
<223> OTHER INFORMATION: oligonucleotide for PCR amplification of
      SV40 promoter

<400> SEQUENCE: 5
ggccatcgat gctagccagc tgtggaatgt gtgtcag                              37

<210> SEQ ID NO 6
<211> LENGTH: 33
<212> TYPE: DNA
<213> ORGANISM: artificial sequence
<220> FEATURE:
<221> NAME/KEY: misc_feature
<222> LOCATION: (1)..(33)
<223> OTHER INFORMATION: oligonucleotide for PCR amplification of
      SV40 promoter

<400> SEQUENCE: 6
ccggaccggt aagcttttg caaaagccta ggc                                   33

<210> SEQ ID NO 7
<211> LENGTH: 31
<212> TYPE: DNA
<213> ORGANISM: artificial sequence
<220> FEATURE:
<221> NAME/KEY: misc_feature
<222> LOCATION: (1)..(31)
<223> OTHER INFORMATION: oligonucleotide for vector construction

<400> SEQUENCE: 7
catgttggct agccatttaa atcctcgagg a                                    31

<210> SEQ ID NO 8
<211> LENGTH: 31
<212> TYPE: DNA
<213> ORGANISM: artificial sequence
<220> FEATURE:
<221> NAME/KEY: misc_feature
<222> LOCATION: (1)..(31)
<223> OTHER INFORMATION: oligonucleotide for vector construction

<400> SEQUENCE: 8
catgtcctcg aggatttaaa tggctagcca a                                    31

<210> SEQ ID NO 9
<211> LENGTH: 44
<212> TYPE: DNA
<213> ORGANISM: artificial sequence
<220> FEATURE:
<221> NAME/KEY: misc_feature
<222> LOCATION: (1)..(45)
<223> OTHER INFORMATION: oligonucleotides used for vector construction

<400> SEQUENCE: 9
ccggtcgtac ggctagccct gcaggtccgg acttaagcgg ccgt                      44
```

```
<210> SEQ ID NO 10
<211> LENGTH: 44
<212> TYPE: DNA
<213> ORGANISM: artificial sequence
<220> FEATURE:
<221> NAME/KEY: misc_feature
<222> LOCATION: (1)..(44)
<223> OTHER INFORMATION: oligonucleotides used for vector construction

<400> SEQUENCE: 10
ctagacggcc gcttaagtcc ggacctgcag ggctagccgt acga                    44

<210> SEQ ID NO 11
<211> LENGTH: 33
<212> TYPE: DNA
<213> ORGANISM: artificial sequence
<220> FEATURE:
<221> NAME/KEY: misc_feature
<222> LOCATION: (1)..(33)
<223> OTHER INFORMATION: oligonucleotide used for RT-PCR amplification
      of Bcl2

<400> SEQUENCE: 11
aattcgtacg accatggcgc acgctgggag aac                                33

<210> SEQ ID NO 12
<211> LENGTH: 32
<212> TYPE: DNA
<213> ORGANISM: artificial sequence
<220> FEATURE:
<221> NAME/KEY: misc_feature
<222> LOCATION: (1)..(32)
<223> OTHER INFORMATION: oligonucleotide used for RT-PCR amplification
      of Bcl2

<400> SEQUENCE: 12
aattgctagc cttcacttgt ggctcagata gg                                 32

<210> SEQ ID NO 13
<211> LENGTH: 32
<212> TYPE: DNA
<213> ORGANISM: artificial sequence
<220> FEATURE:
<221> NAME/KEY: misc_feature
<222> LOCATION: (1)..(32)
<223> OTHER INFORMATION: oligonucleotide used for RT-PCR amplification
      of Dff45

<400> SEQUENCE: 13
aattcgtacg accatggagg tgaccgggga cg                                 32

<210> SEQ ID NO 14
<211> LENGTH: 31
<212> TYPE: DNA
<213> ORGANISM: artificial sequence
<220> FEATURE:
<221> NAME/KEY: misc_feature
<222> LOCATION: (1)..(31)
<223> OTHER INFORMATION: oligonucleotide used for RT-PCR amplification
      of Dff45

<400> SEQUENCE: 14
aattgctagc ctatgtggga tcctgtctgg c                                  31

<210> SEQ ID NO 15
<211> LENGTH: 34
<212> TYPE: DNA
<213> ORGANISM: artificial sequence
<220> FEATURE:
```

```
<221> NAME/KEY: misc_feature
<222> LOCATION: (1)..(34)
<223> OTHER INFORMATION: oligonucleotide used for RT-PCR amplification
      of Bad

<400> SEQUENCE: 15
aattcttaag accatcttcc agatcccaga gttg                              34

<210> SEQ ID NO 16
<211> LENGTH: 29
<212> TYPE: DNA
<213> ORGANISM: artificial sequence
<220> FEATURE:
<221> NAME/KEY: misc_feature
<222> LOCATION: (1)..(29)
<223> OTHER INFORMATION: oligonucleotide used for RT-PCR amplification
      of Bad

<400> SEQUENCE: 16
aattcggccg tcactgggag ggggcggag                                    29

<210> SEQ ID NO 17
<211> LENGTH: 32
<212> TYPE: DNA
<213> ORGANISM: artificial sequence
<220> FEATURE:
<221> NAME/KEY: misc_feature
<222> LOCATION: (1)..(32)
<223> OTHER INFORMATION: oligonucleotide for RT-PCR amplification of
      cide-a

<400> SEQUENCE: 17
aattcttaag accatggagg ccgcccggga ct                                32

<210> SEQ ID NO 18
<211> LENGTH: 30
<212> TYPE: DNA
<213> ORGANISM: artificial sequence
<220> FEATURE:
<221> NAME/KEY: misc_feature
<222> LOCATION: (1)..(30)
<223> OTHER INFORMATION: oligonucleotide for RT-PCR amplification of
      cide-a

<400> SEQUENCE: 18
aattcggccg ctatccacac gtgaacctgc                                   30
```

What is claimed is:

1. A method for obtaining a self-selecting eukaryotic cell stably transfected in vitro with at least two episomes, which comprises
   (a) transfecting a eukaryotic cell with:
      (i) a first episome which comprises (a) an EBV origin of replication (oriP); (b) a nucleic acid sequence encoding a kill agonist wherein expression of said kill agonist in the absence of a kill antagonist results in cell death; and (c) a nucleic acid sequence encoding a selectable marker for eukaryotic cells; and
      (ii) a second episome comprising (a) an EBV origin of replication (oriP); and (b) a nucleic acid sequence encoding a kill antagonist wherein expression of said kill antagonist prohibits the occurrence of cell death resulting from expression of said kill agonist; to produce self-selecting transfected cells whereby exogenous selection factors are not required for continued maintenance and selection of the episomes in said cells and wherein said cells also express an antigen that promotes retention of the episomes by said cells; and
   (b) maintaining said cells under conditions in which said kill agonist, said kill antagonist and said selectable marker are expressed.

2. The method of claim 1 wherein said antigen that promotes retention of the episomes by said cells is EBNA 1 antigen and is expressed from one of said episomes.

3. The method of claim 1 wherein at least one of said episomes further comprises a nucleic acid sequence selected from the group consisting of a nucleic acid sequence encoding a protein desired to be expressed in said cells, a nucleic acid sequence encoding an RNA that is not intended to be translated, and a DNA sequence used as a tag for said cells, and wherein said selectable marker is selected from the group consisting of an antibiotic resistance marker, an essential enzyme, and a second kill antagonist whose expression prohibits the occurrence of cell death resulting from the expression of a second kill agonist that is also encoded by said episome.

4. The method of claim 3 wherein said protein desired to be expressed by said cells is a therapeutic protein and said RNA that is not intended to be translated is a therapeutic RNA.

5. The method of claim 3, wherein:
(a) successful transfection of said eukaryotic cell with said episomes, wherein at least one of said episomes further comprises said nucleic acid sequence encoding said protein or RNA which results in expression of said protein or RNA, also results in expression of said kill antagonist and prohibits said cell death caused by expression of said kill agonist protein; and
(b) unsuccessful transfection of aid eukaryotic cell with said episomes, wherein at least one of said episomes further comprises said nucleic acid sequence encoding aid protein or RNA, does not result in expression of said kill antagonist protein, and does not prohibit said cell death caused by expression of said kill agonist protein.

6. The method of claim 5 wherein said nucleic acid sequence encoding a protein desired to be expressed or RNA and said nucleic acid sequence encoding said kill antagonist protein are contained in an episome transfected into said cell.

7. The method of claim 6 wherein said nucleic acid sequence encoding said kill agonist protein is expressed from said first episome that is transfected into said cell, and wherein said episomes further comprise a nucleic acid sequence that promotes autonomous replication of the episomes in said cell, and wherein said transfected cell expresses one or more proteins that promote nuclear retention of the episomes.

8. The method of claim 7, wherein said episome comprising said nucleic acid sequence encoding said kill agonist protein further comprises a nucleic acid sequence encoding a non-kill antagonist selectable marker.

9. The method of claim 5 wherein said nucleic acid sequence encoding said kill agonist is integrated in the chromosomal DNA of said cell.

10. A method for obtaining a self-selecting eukaryotic cell stably transfected in vitro with at least two episomes, which comprises
(a) transfecting a eukaryotic cell with:
(i) a first episome which comprises (a) an EBV origin of replication (oriP); (b) a nucleic acid sequence encoding a first kill agonist wherein expression of said first kill agonist in the absence of a kill antagonist results in cell death; and (c) a nucleic acid sequence encoding a second kill antagonist, wherein expression of said second kill antagonist prohibits the occurrence of cell death resulting from the expression of a second kill agonist; and
(ii) a second episome comprising (a) an EBV origin of replication (oriP); and (b) a nucleic acid sequence encoding a first kill antagonist wherein expression of said first kill antagonist prohibits the occurrence of cell death resulting from expression of said first kill agonist; and (c) a nucleic acid sequence encoding said second kill agonist, wherein expression of said second kill agonist in the absence of a kill antagonist results in cell death by a mechanism distinct from the mechanism of said first kill agonist; to produce self-selecting transfected cells, whereby exogenous selection factors are not required for continued maintenance and selection of the episomes in said cells and wherein said cells also express an antigen that promotes retention of the episomes by said cells; and (b) maintaining said cells under conditions in which said kill agonists and said kill antagonists are expressed.

11. The method of claim 10, wherein at least one of said episomes further comprises a nucleic acid sequence encoding a third protein the expression of which is desired in said cell, and wherein EBNA-1 is expressed from a nucleic acid sequence contained in said first or said second episome.

12. The method of claim 11, wherein at least one of said episomes further comprises a nucleic acid sequence encoding a non-kill antagonist selectable marker for eukaryotic cells.

13. The method of claim 10 wherein said first and second kill agonists are apoptosis agonists and said first and second kill antagonists are cognate apoptosis antagonists.

14. The method of claim 13 wherein said apoptosis agonists are selected from the group consisting of Bax, Bak, Bad, dff, adenovirus E1a, ice, cad, cide-a, and cide-b.

15. The method of claim 14 wherein said apoptosis antagonists are selected from the group consisting of Bcl2, $Bcl-X_L$, $Bcl-X_S$, adenoE1b, A1 Mcl-1, dff45, CrmA, and icad.

16. A transfected eukaryotic cell in vitro which comprises:
(i) a first episome which comprises (a) an EBV origin of replication; and (b) a nucleic acid sequence encoding a kill agonist, wherein expression of said kill agonist in the absence of a kill antagonist results in cell death; and
(ii) a second episome comprising (a) an EBV origin of replication; and (b) a nucleic acid sequence encoding a kill antagonist, wherein expression of said kill antagonist prohibits the occurrence of cell death resulting from the expression of said kill agonist, wherein said cells are self-selecting and exogenous selection factors are not required for continued maintenance and selection of the episomes in said cells.

17. The eukaryotic cell of claim 16, wherein said first or second episome further comprises a nucleic acid sequence encoding a selectable marker for eukaryotic cells.

18. The eukaryotic cell of claim 16, wherein said first or second episome further comprises a nucleic acid sequence encoding a third protein, and wherein expression of said third protein is desired in said cell.

19. The eukaryotic cell of claim 16, wherein said second episome further comprises a nucleic acid sequence encoding a second kill agonist, and wherein expression of said kill agonist in the absence of a kill antagonist results in cell death and is distinct from said first kill agonist; and wherein said first episome further comprises a nucleic acid sequence encoding a second kill antagonist, and wherein expression of said second kill antagonist prohibits the occurrence of cell death resulting from expression of said second kill agonist.

20. A kit for transfecting eukaryotic cells in vitro with a nucleic acid sequence encoding a protein of interest comprising:
a first episome that comprises a nucleic acid sequence encoding a kill agonist whose expression in the absence of a kill antagonist results in cell death, and
a second episome that comprises a nucleic acid sequence encoding a kill antagonist whose expression prohibits the occurrence of cell death resulting from expression of said kill agonist, wherein said first or second episome comprises an expression cassette for insertion of a nucleic acid sequence encoding a protein or RNA whose expression by said cells is desired.

* * * * *